United States Patent
Lastovich et al.

(10) Patent No.: US 10,273,523 B2
(45) Date of Patent: Apr. 30, 2019

(54) IMAGING CARTRIDGE, PIPETTE, AND METHOD OF USE FOR DIRECT SPUTUM SMEAR MICROSCOPY

(71) Applicant: Becton, Dickinson and Company, Franklin Lakes, NJ (US)

(72) Inventors: Alexander George Lastovich, Raleigh, NC (US); Anita Quinn, Butner, NC (US); Pauline Elizabeth Bell, Wake Forest, NC (US); James Lee Schram, Asheville, NC (US); Rex Young Nielson, Apex, NC (US); Jason Paul Hayes, Heathmont (AU); Matthew James Springer, Melbourne (AU); Lincoln Belcourt, Vermont (AU); Matthew Daniel Solomon, Hughesdale (AU)

(73) Assignee: Becton, Dickinson and Company, Franklin Lakes, NJ (US)

( * ) Notice: Subject to any disclaimer, the term of this patent is extended or adjusted under 35 U.S.C. 154(b) by 475 days.

(21) Appl. No.: 14/787,668

(22) PCT Filed: Apr. 28, 2014

(86) PCT No.: PCT/US2014/035677
  § 371 (c)(1),
  (2) Date: Oct. 28, 2015

(87) PCT Pub. No.: WO2014/179215
  PCT Pub. Date: Nov. 6, 2014

(65) Prior Publication Data
  US 2016/0076072 A1   Mar. 17, 2016

Related U.S. Application Data

(60) Provisional application No. 61/817,158, filed on Apr. 29, 2013.

(51) Int. Cl.
  *G01N 1/28* (2006.01)
  *C12Q 1/24* (2006.01)
  (Continued)

(52) U.S. Cl.
  CPC .............. *C12Q 1/24* (2013.01); *B01L 3/0217* (2013.01); *B01L 3/502* (2013.01); *B01L 3/508* (2013.01);
  (Continued)

(58) Field of Classification Search
  CPC ......... B01L 2200/027; B01L 2200/025; B01L 3/502715; G01N 1/2813
  See application file for complete search history.

(56) References Cited

U.S. PATENT DOCUMENTS 5,597,532 A * 1/1997 Connolly ................ B01L 3/545
  422/401
2002/0057991 A1   5/2002 Kelly et al.
  (Continued)

FOREIGN PATENT DOCUMENTS

RU    2282196 C2    8/2006
WO    2010091080 A2  8/2010

OTHER PUBLICATIONS

International Search Report for Application No. PCT/US2014/035677 dated Oct. 6, 2014.
(Continued)

*Primary Examiner* — Jonathan M Hurst
(74) *Attorney, Agent, or Firm* — Botos Churchill IP Law LLP

(57) ABSTRACT

An assembly for preparing a specimen is provided that may be configured to determine the presence of at least one microorganism specie in the specimen. The assembly may include a pipette configured to acquire a specimen from a sample and an imaging cartridge configured to be in fluid
(Continued)

communication with the pipette. The imaging cartridge and the pipette may be configured to be irreversibly coupled such that the specimen is bio-contained within the imaging cartridge and the pipette when the imaging cartridge and pipette are coupled together. Associated methods of use are also provided.

18 Claims, 16 Drawing Sheets

(51) Int. Cl.
    *B01L 3/00*         (2006.01)
    *G01N 35/00*      (2006.01)
    *B01L 3/02*         (2006.01)
    *G01N 1/30*        (2006.01)
    *A61B 10/00*      (2006.01)

(52) U.S. Cl.
    CPC .............. *G01N 1/2813* (2013.01); *G01N 1/30* (2013.01); *G01N 35/00029* (2013.01); *A61B 10/0051* (2013.01); *B01L 3/502715* (2013.01); *B01L 2200/027* (2013.01); *B01L 2200/10* (2013.01); *B01L 2200/16* (2013.01); *B01L 2300/0636* (2013.01); *B01L 2300/087* (2013.01); *B01L 2400/0481* (2013.01); *B01L 2400/0683* (2013.01); *G01N 2035/00099* (2013.01)

(56) References Cited

U.S. PATENT DOCUMENTS

| | | |
|---|---|---|
| 2003/0186456 A1 | 10/2003 | Stroup |
| 2003/0190259 A1 | 10/2003 | Alley |
| 2004/0082878 A1* | 4/2004 | Baldwin ............ A61B 10/0051 600/573 |
| 2005/0227370 A1* | 10/2005 | Ramel ..................... C12Q 1/00 436/514 |
| 2005/0232813 A1 | 10/2005 | Karmali |
| 2006/0088895 A1 | 4/2006 | Wanders et al. |
| 2006/0257993 A1 | 11/2006 | McDevitt et al. |
| 2007/0292941 A1 | 12/2007 | Handique et al. |
| 2008/0273918 A1 | 11/2008 | Linder et al. |
| 2010/0050789 A1 | 3/2010 | Stroup |
| 2010/0055668 A1 | 3/2010 | Stroup |
| 2010/0291588 A1 | 11/2010 | McDevitt et al. |
| 2011/0020195 A1 | 1/2011 | Luotola |
| 2011/0183433 A1* | 7/2011 | Motadel ................ B01L 3/0275 436/180 |
| 2011/0212440 A1 | 9/2011 | Viovy et al. |
| 2012/0149603 A1 | 6/2012 | Cooney et al. |
| 2012/0201726 A1 | 8/2012 | Pearcy et al. |

OTHER PUBLICATIONS

Summons to Attend Oral Proceedings issued in corresponding EP application No. 14727319.7 on Apr. 26, 2018.

* cited by examiner

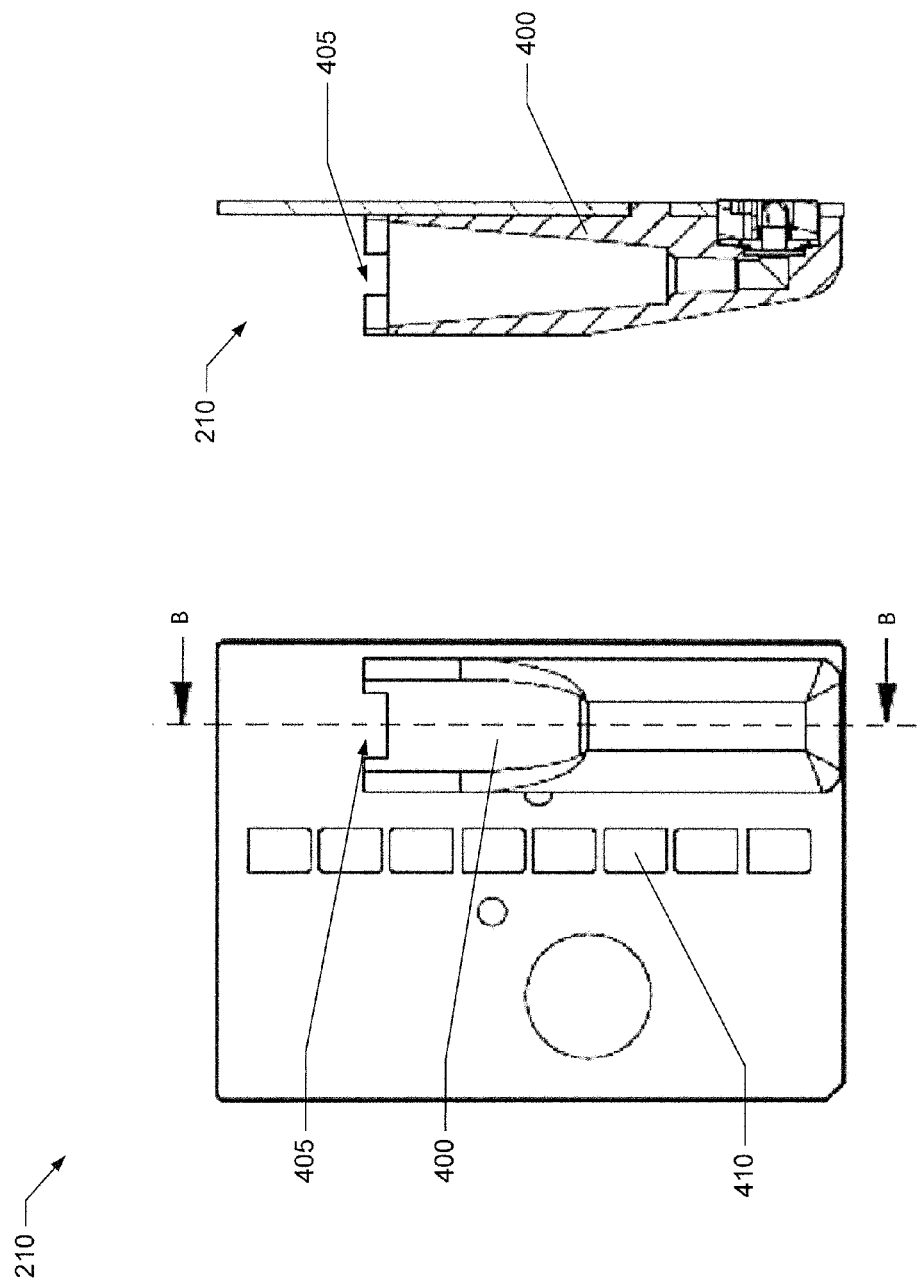

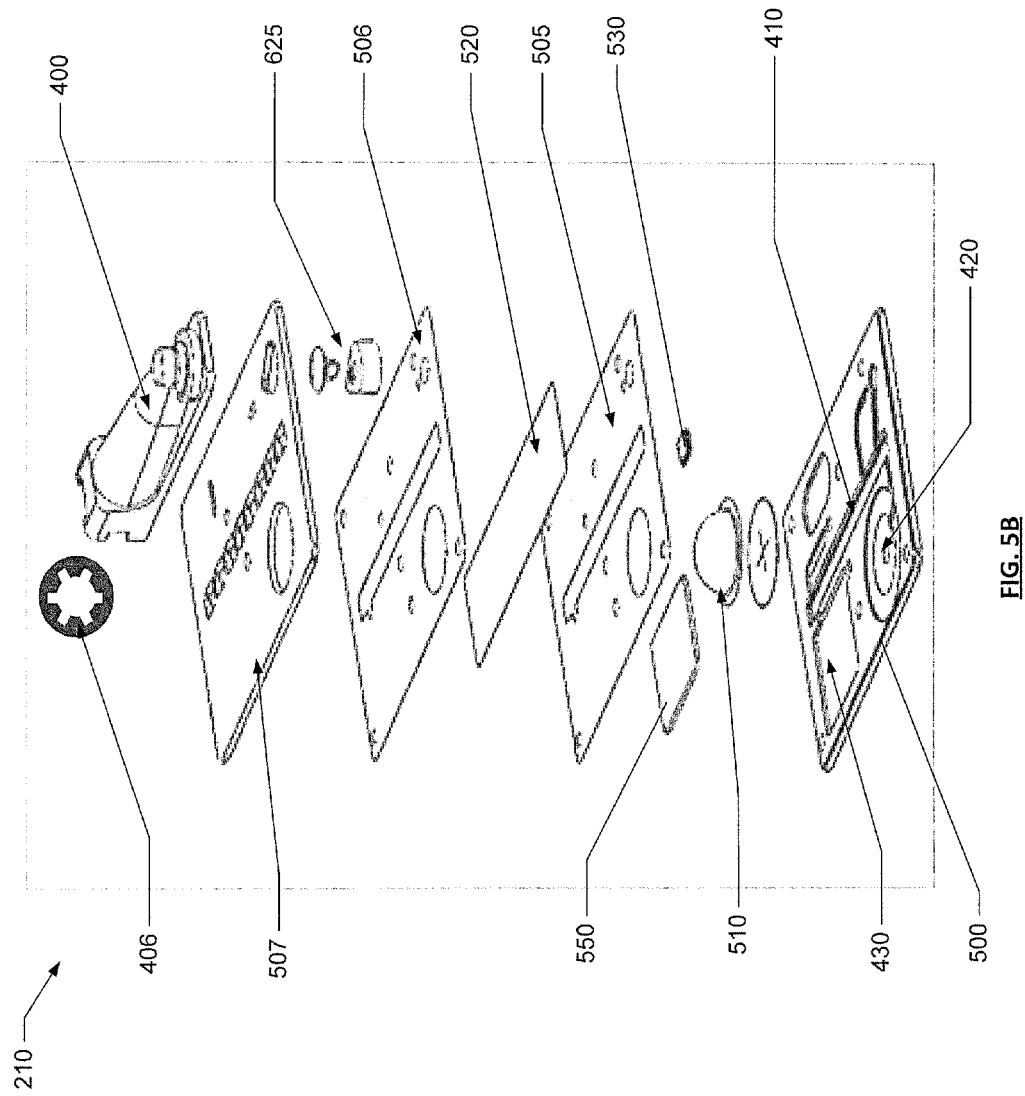

IMAGING CARTRIDGE, PIPETTE, AND METHOD OF USE FOR DIRECT SPUTUM SMEAR MICROSCOPY

CROSS-REFERENCE TO RELATED APPLICATIONS

The present application is a national stage entry under 35 U.S.C. § 371 of International Application No. PCT/US2014/035677 filed Apr. 28, 2014, published in English, which claims priority from U.S. Provisional Patent Application No. 61/817,158 filed Apr. 29, 2013, all of which are incorporated herein by reference.

TECHNICAL FIELD AND BACKGROUND OF THE INVENTION

Embodiments of the present invention relate generally to assemblies and methods for preparing, analyzing, and detecting acid-fast bacilli with sputum smear microscopy. Effective analysis of microscopic images is essential in pathology. In low-income and developing countries, access to expensive microscopy methods and apparatuses is limited. Accordingly, direct microscopy from an unprocessed sputum smear is a primary method for detecting acid-fast bacilli when diagnosing a patient with pulmonary tuberculosis. Direct sputum smear microscopy can be an inexpensive and efficient method for diagnosing a patient with pulmonary tuberculosis, but has inherent drawbacks, such as low and variable sensitivity. Poor sensitivity may be attributed to the variable quality of the testing methods, inadequate sample sizes, unavailability of necessary equipment or supplies, and/or overworked and/or undertrained technicians. A need exists for a system and method for detecting acid-fast bacilli that is more efficient and inexpensive while being accurate and easily performed without specialized training.

BRIEF SUMMARY

Various embodiments of the present invention are directed towards an assembly for preparing a specimen for determining the presence of at least one microorganism specie in the specimen (e.g., an acid-fast *bacillus*). In one embodiment, the assembly may comprise a pipette configured to acquire a specimen from a sample. According to some embodiments, the assembly may further comprise an imaging cartridge configured to be in fluid communication and irreversibly coupled with the pipette such that the specimen is bio-contained therein.

According to one embodiment, the pipette may comprise an inlet, a sampling chamber, and a shaft disposed therebetween. The imaging cartridge may comprise a pipette dock configured to at least partially receive the pipette shaft therein and irreversibly couple thereto. In addition, the pipette may be configured to be in fluid communication with the imaging cartridge upon depression of the sample chamber of the pipette.

In one embodiment, an imaging cartridge is provided for preparing a specimen for determining an amount of at least one microorganism specie. The imaging cartridge may comprise a pipette dock configured to couple to a pipette containing a specimen such that the specimen is bio-contained therein. In addition, the imaging cartridge may comprise at least one reagent for preparing the specimen for imaging. The imaging cartridge may comprise an imaging chamber configured to be in fluid communication with the pipette, wherein the prepared specimen is configured to be spread in the imaging chamber for obtaining an image thereof.

According to another embodiment, the imaging cartridge may further comprise at least one valve disposed between the imaging chamber and the pipette, wherein the at least one valve is configured to allow a specimen to flow from the pipette to the imaging cartridge when the pipette is coupled to the imaging cartridge. In some embodiments, the valve may be further configured to provide for the self-metering of a specimen sample by providing a specimen sample from the pipette to the imaging chamber when a pipette sampling chamber is depressed and by providing for the return of the specimen sample from the imaging chamber to the pipette when the pipette sampling chamber is released. In some embodiments, the imaging cartridge may further comprise at least one channel defined between the imaging chamber and the pipette, wherein the channel is configured to provide for the fluid communication therebetween. The imaging cartridge may further comprise a cartridge blister chamber that is in fluid communication with the imaging chamber. In some embodiments, the cartridge blister chamber may comprise a cartridge blister, wherein the cartridge blister comprises at least one decolorizer reagent therein. According to some embodiments, the cartridge blister may be configured to release the at least one decolorizer reagent therein when a force is applied to the cartridge blister. Further, the imaging cartridge may comprise a fluid trap, such as a wicking chamber in fluid communication with the imaging chamber, wherein the fluid trap is configured to remove excess decolorizer reagent from the imaging chamber.

In some embodiments, the imaging cartridge may comprise indicia configured to provide information indicating an amount of specimen provided to the imaging chamber. The imaging cartridge may further comprise a porous imaging chamber cover configured to permit the specimen within the imaging chamber to dry and prevent biological agents in the specimen from passing through the imaging chamber cover. In some embodiments, the imaging chamber cover may comprise a hydrophobic membrane material. The imaging cartridge may further comprise a magnet disposed within the imaging chamber. The magnet may be configured to move from one end of the imaging chamber to an opposite end of the imaging chamber for spreading the specimen therein. In some embodiments, the imaging cartridge may further comprise any magnetic material disposed within the imaging chamber, wherein the magnetic material is configured to move from a first end to an opposite end of the imaging chamber when a magnetic force is applied thereto for spreading the specimen within the imaging chamber.

Some embodiments of the present invention may provide a pipette for obtaining a specimen. The pipette may comprise an inlet, a sampling chamber, and a shaft disposed therebetween. The pipette may further comprise at least one staining reagent contained within the sampling chamber. In addition, the pipette may be configured to draw in a specimen through the inlet and the shaft and into the sampling chamber upon actuation of the sampling chamber. In one embodiment, the pipette may comprise at least one staining reagent disposed on an interior surface of the sampling chamber. In another embodiment, the pipette may comprise at least one staining reagent that is a dehydrated film of material disposed on the interior surface of the sampling chamber. According to a particular embodiment, the staining compound may comprise Auramine O powder. In some embodiments, the staining compound may be further configured to provide for the liquefaction of the specimen. As such, according to some embodiments, the staining compound may comprise sodium hydroxide and trisodium citrate and/or N-acetyl-L-cysteine. The pipette may further comprise a pipette sachet disposed within the sampling chamber, wherein the pipette sachet comprises at least one rehydrating reagent. The pipette may further comprise a pipette sachet comprising at least one solvent reagent configured to rehydrate and/or re-dissolve the staining compound upon mixing with the solvent reagent. In addition, the pipette sachet may be configured to release the solvent reagent when a force is applied thereto, the force causing the pipette sachet to at least partially rupture. According to some embodiments, the pipette may be configured to dispense the specimen out of the inlet upon actuation of the sampling chamber.

Another embodiment of the present invention may provide a method of preparing a specimen for determining the presence of at least one microorganism specie in the specimen. The method may comprise obtaining a specimen with a pipette and irreversibly coupling the pipette with an imaging cartridge such that the specimen is bio-contained therein. The method may comprise staining the specimen with a staining compound disposed within the pipette. According to one embodiment, the method may comprise dispensing a desired amount of the stained specimen from the pipette into an imaging chamber defined in the imaging cartridge. The method may further comprise spreading the stained specimen within the imaging chamber. In addition, the method may comprise drying the stained specimen within the imaging chamber. In some embodiments, the method may comprise dispensing a decolorizer reagent into the imaging chamber. Further, the method may include removing excess decolorizer reagent from the imaging chamber. In addition, the method may include acquiring an image of the specimen in the imaging chamber. Further, the method may include comprising determining whether acid-fast bacilli are present in the specimen.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 4B illustrates a top view of an imaging cartridge configured to be coupled with a pipette for processing a sample according to some embodiments of the present invention;

FIG. 4C illustrates a cross-sectional view of the imaging cartridge shown in FIG. 4B along the line B-B according to some embodiments of the present invention;

FIG. 5B illustrates an exploded view of the imaging cartridge according to some embodiments of the present invention;

DETAILED DESCRIPTION OF THE INVENTION

Embodiments of the present invention will now be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. To the extent used herein, the terms top, bottom, side, up, down, upwards, downwards, vertical, horizontal, and the like do not imply a required limitation in all embodiments of the present invention, but rather are used herein to help describe relative direction or orientation in the example embodiments illustrated in the figures.

Various embodiments of the present invention generally provide for an assembly to prepare, analyze, and detect a specie in a sample or specimen. For example, the specie may be indicated by one or more reagents. In some embodiments, the assembly may be configured to facilitate detection of a microorganism specie, such as acid-fast bacilli, using direct sputum smear microscopy. The amount and/or presence of the specie may be determined by analyzing images of the sample that are captured using an image acquisition device. According to some embodiments, the assembly is a sealed container and/or cartridge that is closed to the outside environment so as to be bio-contained such that contamination of the sample from the outside environment is limited and/or the outside environment is limited from exposure to the contents of the assembly, cartridge, and/or pipette. As such, embodiments of the present invention may provide advantages over the prior art, such as reducing contamination of the sample and exposure to the user. Additionally and/or alternatively, embodiments of the present invention may provide advantages over the prior art, such as providing standardized testing of samples, providing a minimal cost solution for testing samples, and/or providing a solution for testing samples requiring minimal time, training, and/or instruction.

Figure 1:
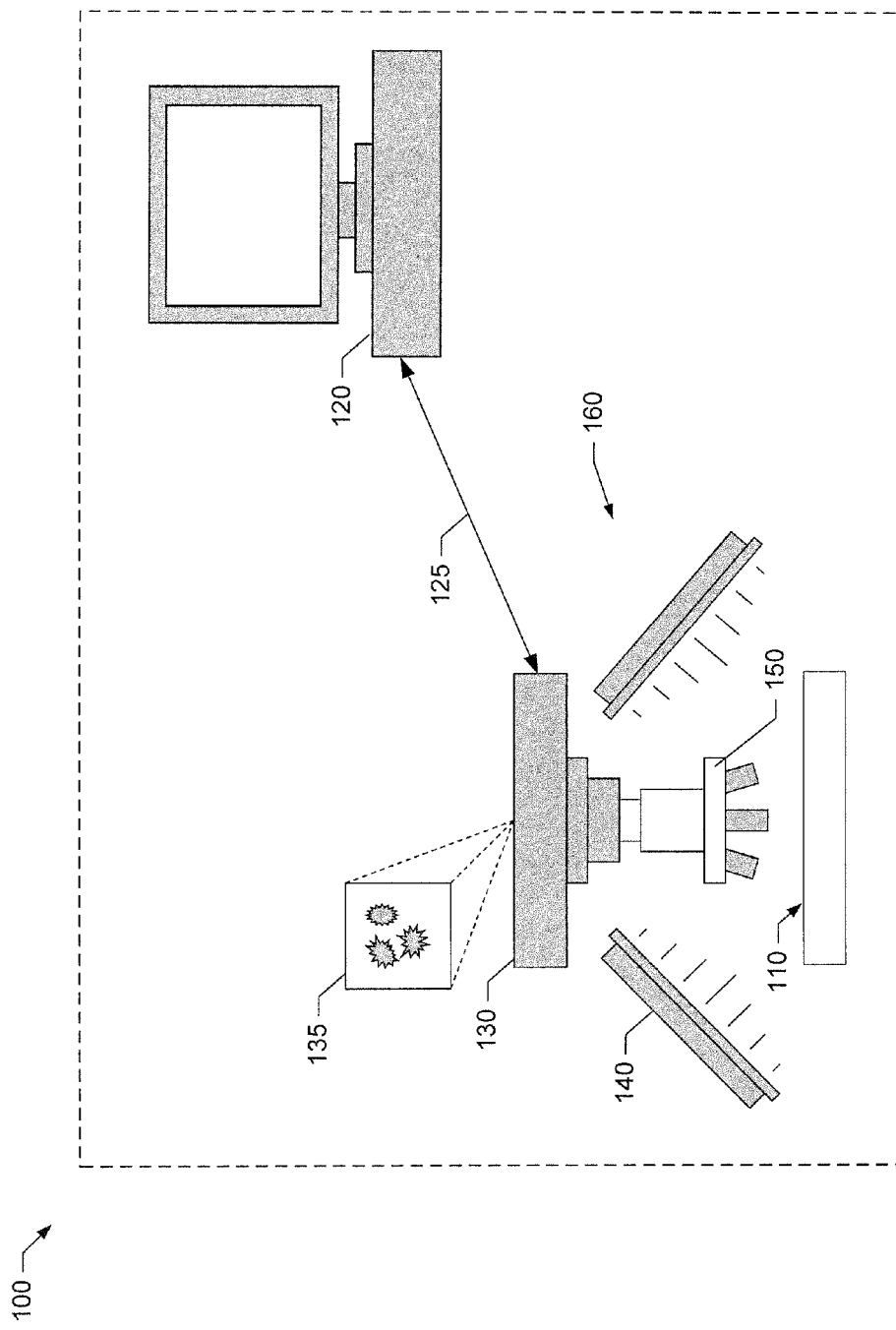
FIG. 1 illustrates a system for detecting a specimen within a sample according to some embodiments of the present invention.

According to one embodiment, FIG. 1 illustrates a system 100 for detecting acid-fast bacilli using sputum smear microscopy. In this regard, a system 100 generally comprises a microscope 160 having an illumination source 140 and a magnifying objective 150, a cartridge assembly 110, a computing device 120, an image acquisition device 130, and a data transmission link 125 between the computing device 120 and the image acquisition device 130. In some embodiments, the image acquisition device 130 may be configured to capture a plurality of images 135 of a sample disposed within a cartridge assembly 110. The image acquisition device 130 may operably engage the microscope 160 and in one embodiment, comprises a CCD camera, which could provide black and white or color images. According to some embodiments, the image acquisition device 130 may comprise a CMOS camera, which may be configured to provide black and white images and/or color images. Typically, such an image acquisition device 130 may include an associated frame grabber (not shown) to facilitate image capture, both the image acquisition device 130 and the associated frame grabber being referred to herein as the "image acquisition device 130" for convenience. In some instances, both the image acquisition device 130 and the microscope 160 may be replaced by, for example, a linear flat scanner and a controlled illumination source. Though different configurations of the system 100 are contemplated by embodiments of the present invention, various embodiments will be described herein in terms of the image acquisition device 130 and the associated microscope 160. Accordingly, one skilled in the art will understand and appreciate the capabilities and methodologies associated with these different configurations for accomplishing embodiments of the present invention as detailed herein. Further, although the present embodiments disclose an image acquisition device as a CCD camera, it is understood that the image acquisition device may be any device configured to capture an image, such as a camera, a scanner, and/or any device configured to capture a plurality of images. In one embodiment, the image acquisition device is a fluorescent microscope. According to some embodiments, the image acquisition device may be configured as an external fluorescent microscope. In some embodiments, the image acquisition device may be configured as an epifluorescence microscope. The image acquisition device may be capable of capturing low and/or high resolution images at any desired magnification, various regions of interest, and/or within various fields of view that may correspond to all or a portion of the sample and/or cartridge assembly 110.

The image acquisition device 130 may be capable of transmitting image data via the data transmission link 125 to the computing device 120. Accordingly, the computing device 120 may be configured to determine the presence of a microorganism specie, such as an acid-fast bacilli, based at least in part on the image data of the acquired images of the sample. According to one embodiment, the computing device 120 may be configured to use optical image acquisition algorithms to automatically determine the amount and/or presence of the microorganism specie. For example, the cartridge assembly 110 may be imaged through an automated process via the image acquisition device 130, transmission data link 125 and/or the computing device 125.

According to some embodiments, the image acquisition device 130, transmission data link 125, and/or computing device 125 may be integrated into a single apparatus. Additionally and/or alternatively, the cartridge assembly 110 may be used in cooperation with a manual process wherein a user acquires an image of the sample within the cartridge assembly 110 and visually inspects the acquired image of the sample to determine the presence of a microorganism specie.

The image acquisition device 130 is generally configured to capture a plurality of images 135 of a sample disposed within a cartridge assembly 110 through a magnifying objective 150, wherein the images 130 may further comprise a digital image having corresponding image data, collectively referred to herein as "the image 135." According to some embodiments, the sample and/or cartridge assembly 110 may be illuminated by an illumination source 140. Accordingly, the images 135 of the sample and/or cartridge assembly 110 may be captured by image acquisition device 130. Additionally and/or alternatively, the image acquisition device 130 may be configured to communicate with the computing device 120 via a data transmission link 125, which may provide for wired and/or wireless communication between the image acquisition device 130 and the computing device 120. In some embodiments, the computing device 120 may be configured to analyze the image 135 for the presence of acid-fast bacilli, based at least in part on detection of regions of interest of the image 135. One skilled in the art will appreciate that the computing device 120 may be any suitable processor device or processing element configured to communicate with the image acquisition device and is further configured to analyze a plurality of images as described herein.

Figure 2:
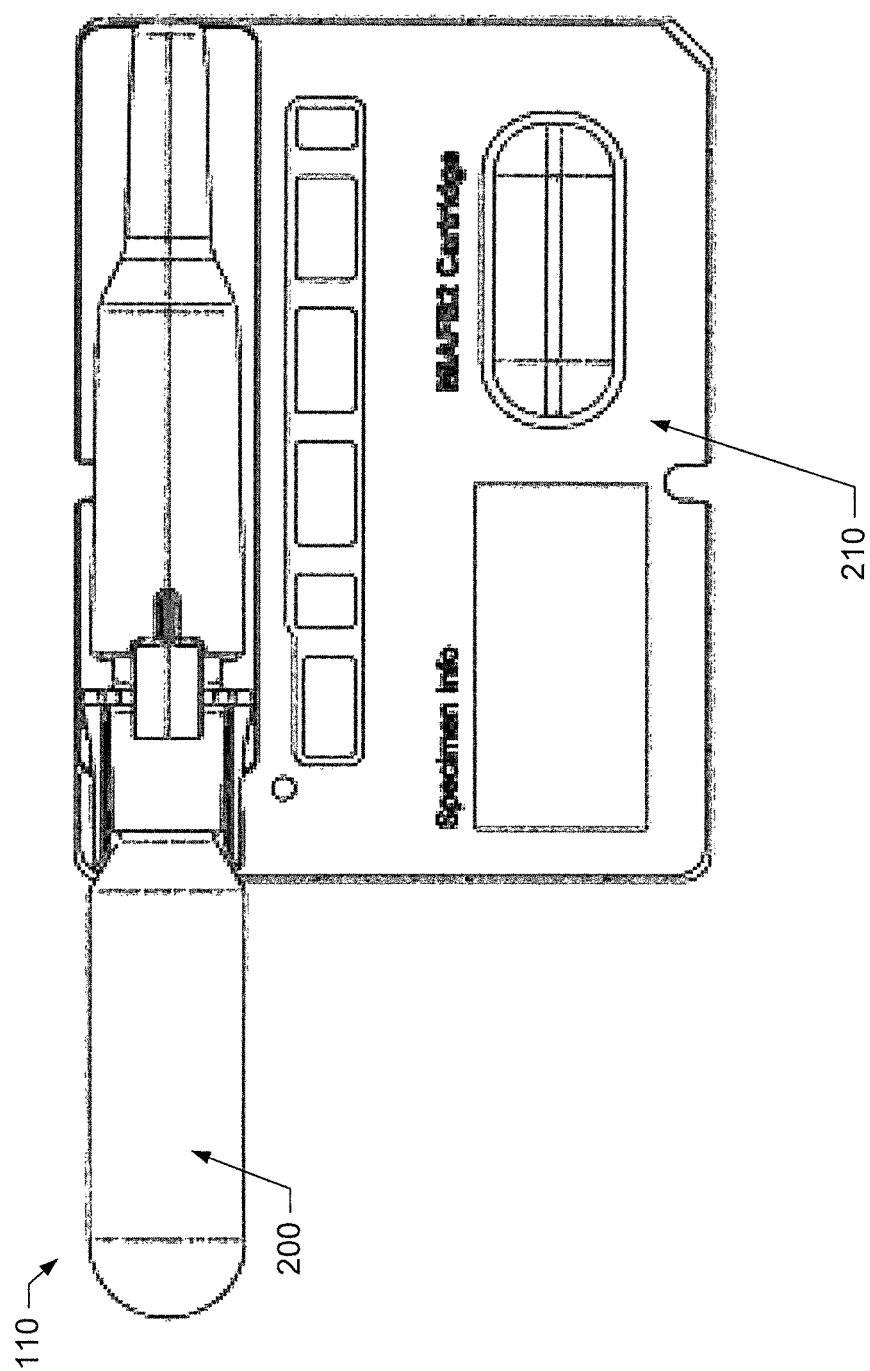
FIG. 2 illustrates a cartridge assembly according to some embodiments of the present invention.

In some embodiments of the present invention, the system 100 may further comprise a cartridge assembly 110, which may include a pipette 200 and an imaging cartridge 210, as shown in FIG. 2. The cartridge assembly 110 may be configured to be a closed or bio-contained assembly. Specifically, the coupling of a pipette 200 to an imaging cartridge 210 may create a biologically contained system configured to limit the introduction or release of any foreign biological material into or out of the cartridge assembly 110. According to some embodiments, the cartridge assembly 110 may include filter membranes and/or the like disposed proximate to any openings of the cartridge assembly such that potentially hazardous bacteria-sized particles or bio-contaminants in the specimen are prevented, limited, and/or impeded from passing through the openings and out of the cartridge assembly, while allowing for gaseous material to pass through the openings to relieve any pressure buildup. In an instance where the system 100 acquires images 135 of a sample and/or the cartridge assembly 110, the cartridge assembly 110 may be configured to receive a pipette 200 such that the pipette 200 is engaged with the imaging cartridge 210. According to some embodiments, the system 100 may be adapted to receive an imaging cartridge 210 therein such that insertion of the imaging cartridge 210 aligns the imaging cartridge 210 with the microscope 160 and/or image acquisition device 130 for capturing a plurality of images of a sample. Although the imaging cartridge 210 may be different sizes and configurations as explained in further detail below, according to one exemplary embodiment, the imaging cartridge is about 70-80 mm in length, about 50-60 mm in width, and about 20 mm in thickness. In some embodiments, the cartridge assembly 110 may be approximately 100 mm in length when the pipette 200 is engaged with the imaging cartridge 210. According to one embodiment, the cartridge assembly 110 may be approximately 115 mm in length when the pipette 200 is engaged with the imaging cartridge 210.

Figure 3:
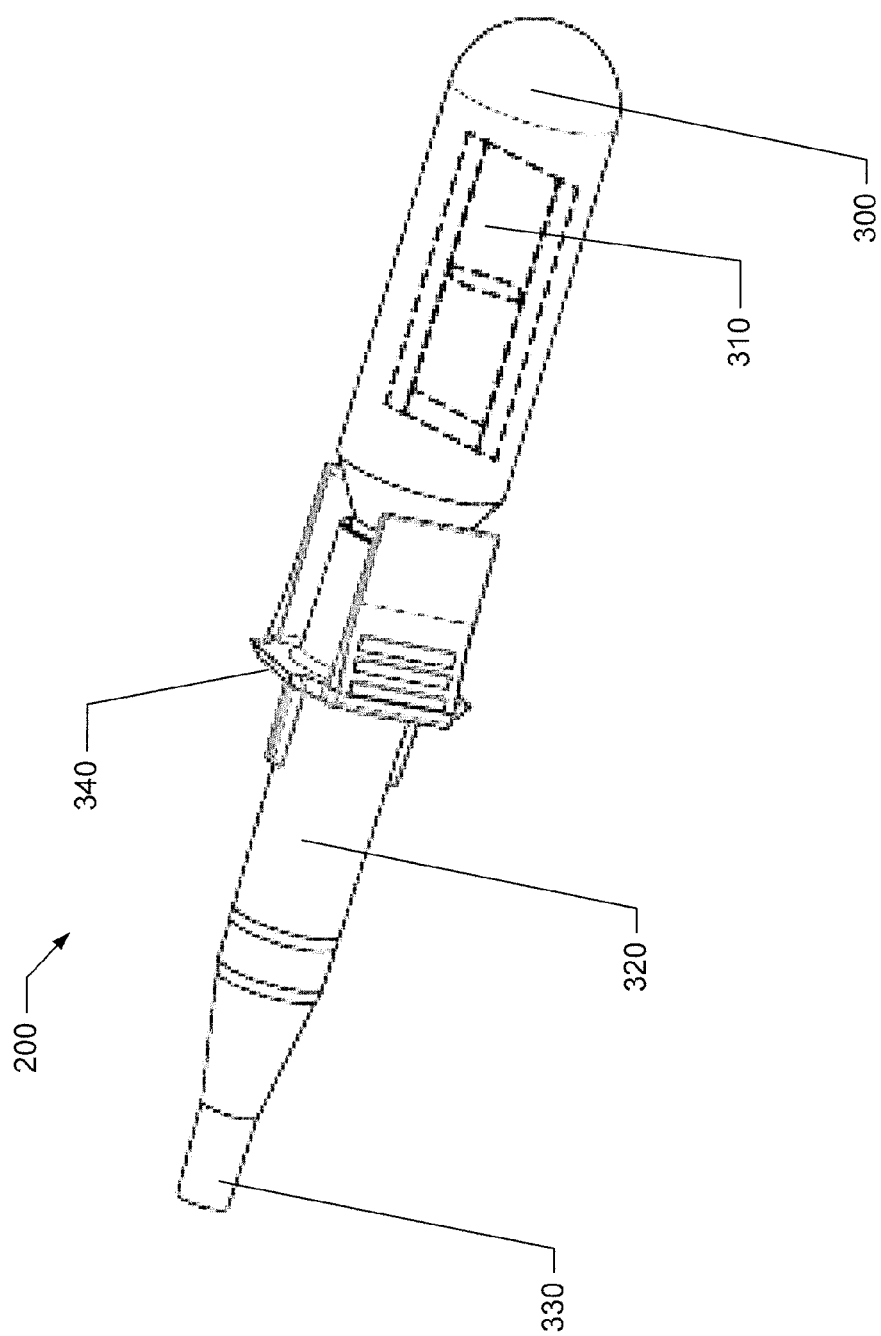
FIG. 3 illustrates a pipette configured to collect a specimen sample according to some embodiments of the present invention.
Figure 4A:
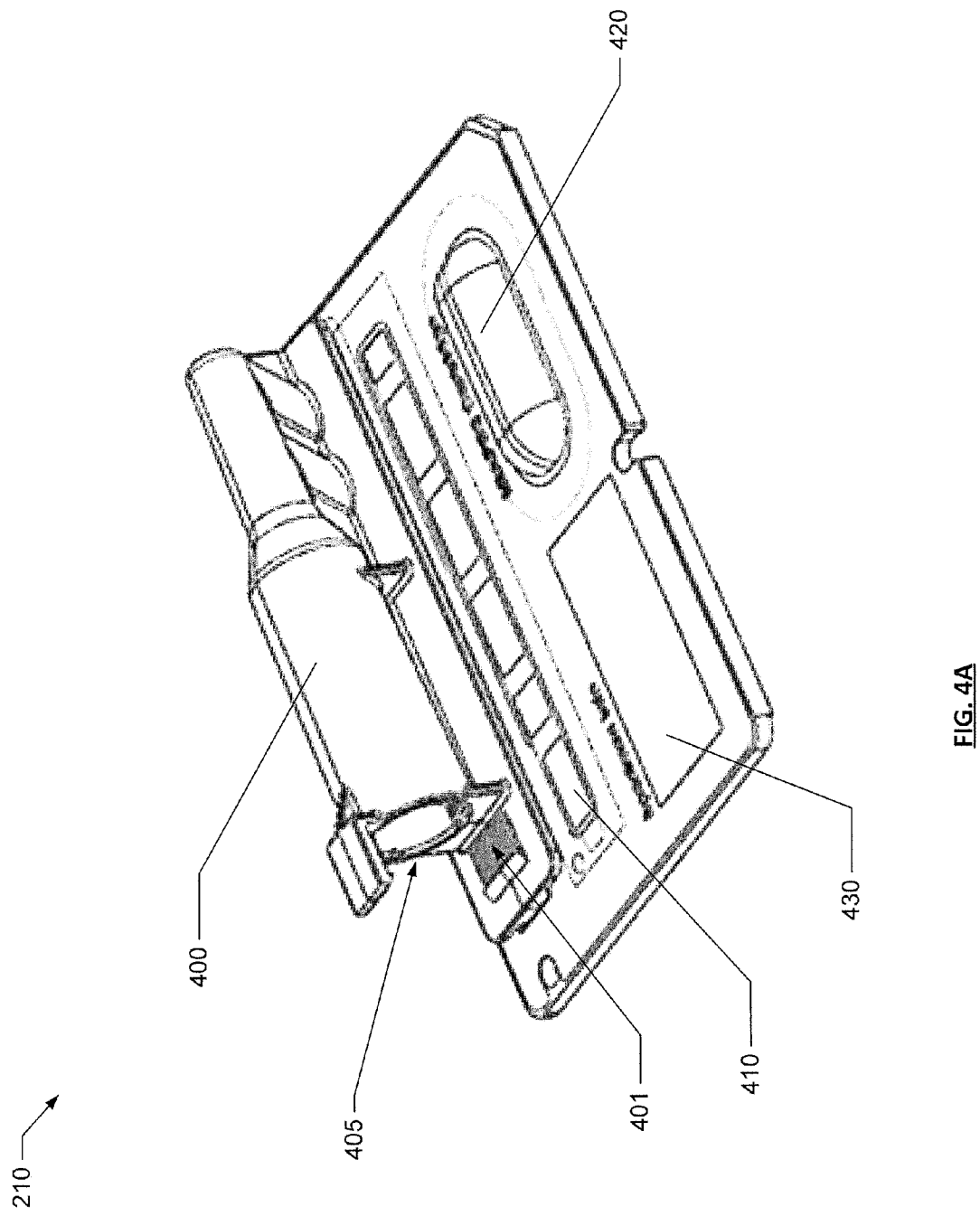
FIG. 4A illustrates an imaging cartridge configured to be coupled with a pipette for processing a sample according to some embodiments of the present invention.
Figure 9:
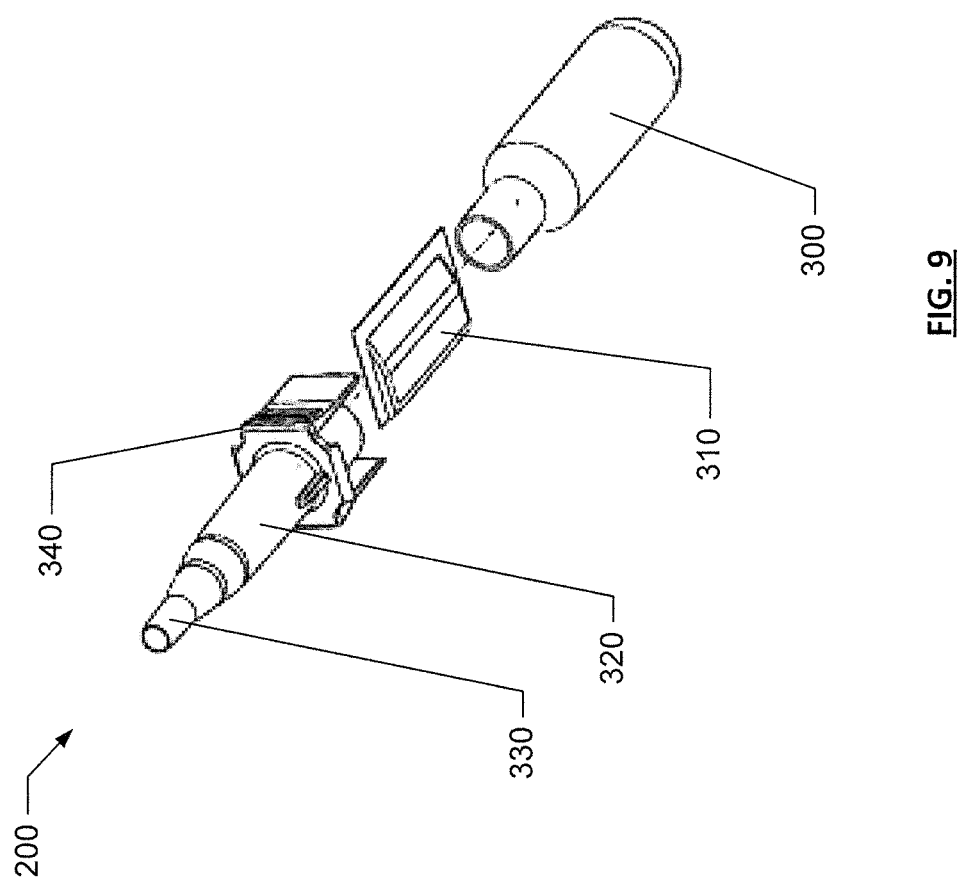
FIG. 9 illustrates an exploded view of a pipette configured to collect a specimen sample according to other embodiments of the present invention.

According to some embodiments, the pipette 200 may be configured to acquire a biological sample containing sputum. As shown in FIGS. 3 and 9, the pipette 200 may include a pipette inlet 330, a pipette shaft 320, a sampling chamber 300, and a pipette sachet 310. In some embodiments, the pipette may have a total length defined by the length of the sampling chamber 300, the pipette shaft 320 and the pipette inlet 330. According to one embodiment, the pipette may be approximately 50-60 mm in length. In some embodiments, the pipette may be approximately between 85 and 100 mm in length. Although the length of the pipette may vary, one skilled in the art may appreciate that embodiments of the present invention may include a pipette having an appropriate length such that the pipette may adequately receive a sputum sample from a 50 mL conical collection tube, yet short enough to allow for a viscous sample to travel into the pipette inlet 330, up the pipette shaft 320, and into the sampling chamber 300 for further processing and/or analysis. According to some embodiments, the pipette shaft 320 may be marked such that a user may readily determine the amount of sputum sample being acquired by the pipette 200 during a metering process. For example, the pipette shaft 320 may include graduation marks indicating increasing volume measurements as the marks extend from the pipette inlet 330 to the sampling chamber 300. In some embodiments, the pipette shaft 320 may include at least two graduation marks indicating a minimum and maximum volume for measuring an amount of the specimen sample.

According to a particularly advantageous aspect of some embodiments of the present invention, the pipette 200 may include a pipette inlet 330 that provides for adequate sampling of a sputum sample. A viscous sputum sample may be difficult to aspirate with a pipette having a narrow inlet. Accordingly, embodiments of the present invention may provide a pipette having a pipette inlet 330 that may include a tip having an opening slightly larger than typical syringe tip openings. For example, the inlet 330 may be about 3-5 mm in diameter. In some embodiments, the pipette inlet 330 may define a bladed edge opening configured to cut, separate, and/or sample a sputum sample. As such, the pipette enables a user to adequately obtain even the most viscous sputum, which is the desired portion of the sample to be analyzed. In addition, the pipette inlet 330 and pipette shaft 320 may be shaped to be received by the imaging cartridge 210 such that insertion of the pipette inlet 330 and pipette shaft 320 into a pipette dock 400 of the imaging cartridge 210 is irreversible once the imaging cartridge 210 and the pipette 200 are coupled. For example, the coupling of the pipette 200 and the imaging cartridge 210 may be irreversible such that applying a force opposite to the insertion direction to remove the pipette 200 from the imaging cartridge 210 is insufficient. In other embodiments, the coupling of the pipette 200 and the imaging cartridge 210 may be a simple snap configuration. In each embodiment, a fluid seal is created and maintained between the pipette tip and the pipette dock 400. According to one embodiment, the pipette 200 may be coupled with the imaging cartridge via a threaded, snap-fit, or force-fit connection. As such, the connection may prohibit the pipette 200 from disengaging the imaging cartridge 210 from a force opposite to the insertion direction. In another embodiment, the pipette dock 400 may include a retention washer or detent such that insertion of the pipette inlet 330 and the pipette shaft 320 into the pipette dock 400 engages the retention washer or detent to lock the pipette 200 to the imaging cartridge 210.

In some embodiments, the pipette dock 400 may include a ratchet mechanism configured to engage the pipette 200. For example, the pipette dock may include a plurality of raised teeth 401 configured to engage with at least one corresponding tooth 340 defined by the pipette 200. As such, when the pipette 200 is coupled with the imaging cartridge 210, the at least one tooth 340 may engage the plurality of raised teeth 401 such that, once engaged, the pipette may only be allowed to move in a direction towards the pipette dock. Accordingly, once the at least one tooth 340 and the plurality of raised teeth 401 are engaged, the pipette 200 may be inserted into the pipette dock 400, but may not be removed from the pipette dock.

In some embodiments, the pipette dock 400 may include a washer 406, as shown in FIG. 5B. Specifically, the washer 406 may be disposed within the pipette dock 400 and may be configured to engage the pipette 200 when the pipette 200 is inserted within the pipette dock 400. Accordingly, the washer 406 may be "star" shaped and configured to clamp, "bite", and/or otherwise engage the pipette 200 when the pipette 200 is inserted into the pipette dock 400 such that the pipette 200 cannot be removed from the pipette dock 400 once the star washer 406 has engaged the pipette 200. In some embodiments, when the pipette 200 is engaged and inserted within the pipette dock 400, the pipette dock 400 may be configured to enclose a portion of the pipette used to obtain the specimen sample. As such, the pipette dock 400 may cover and may minimize access to the portion of the pipette 200 used to obtain the specimen sample, thereby advantageously minimizing the risk of contaminating the environment with the specimen sample.

Some embodiments may include a pipette 200 further comprising a sampling chamber 300. A sample of viscous sputum may be metered into the pipette 200 via the pipette inlet 330. This may be accomplished by depressing the pipette chamber 300, without rupturing the sachet, to create a vacuum for drawing a sample through the pipette inlet 330 and pipette shaft 320 and into the pipette chamber. Further, the amount of sample being metered may be measured by graduation marks provided by the pipette shaft 320 as the sample enters the pipette shaft 320. Once the sample has been metered into the pipette 200 and the pipette is coupled with the imaging cartridge 210, the sample may be stained, liquefied, and/or processed to determine the presence of acid-fast bacilli. In another embodiment, the amount of sample being metered may be measured after the pipette has been coupled with the cartridge, after the sample has been stained, liquefied and/or otherwise processed, and/or upon the transferring of the sample from the pipette to the imaging cartridge. In some embodiments, the amount of sample being metered may be measured within the imaging cartridge itself, as discussed in greater detail herein.

According to one advantageous aspect of the present invention, a pipette sachet 310 is disposed within the sampling chamber 300. In some embodiments, the pipette sachet 310 may include a staining compound configured to stain and/or liquefy the viscous sputum sample. Additionally and/or alternatively, the sampling chamber 300 may include a staining compound configured to stain and/or liquefy the viscous sputum sample. In some embodiments, the staining compound may include a film of dried-down Auramine O powder that is applied along the interior surface of the sampling chamber 300. According to some embodiments, the interior surface of the sampling chamber 300 may include the dried-down staining compound and the pipette sachet 310 may include a liquefaction reagent configured to provide for the liquefaction of the staining compound and/or the viscous sputum sample. In some embodiments, the liquefaction reagent may comprise sodium hydroxide and trisodium citrate. According to some embodiments, the sampling chamber 300 may include approximately 200 µL of a solution containing 2% sodium hydroxide, 1.45% trisodium citrate may be combined with 100 µL of approximately between 0.5 mg/mL and 10 mg/mL Auramine O dissolved in 70% ethanol, which is subsequently dried down to produce a staining compound that covers the interior surface of the sampling chamber 300. In other embodiments, dithiothreitol (DTT), bleach, other reductants, or another substance configured to liquefy sputum may be used. Additionally, the pipette sachet 310 may include a reagent comprising 300 µL of 70% ethanol diluted with water. In some embodiments, the pipette sachet 310 may include a reagent comprising 300 µL of approximately between 20-70% ethanol diluted with water.

The pipette sachet 310 may be configured to release the reagent once ruptured. Once the pipette sachet 310 is ruptured and the reagent contents disposed therein are released into the sampling chamber 300, the reagent mixes with the staining compound and the sputum sample disposed within the sampling chamber so as to stain and/or liquefy the sputum sample for further processing. The reagent may assist in the rehydration of the staining compound, which may produce a stained sample of sputum comprising approximately 2 parts of the sputum sample and 3 parts of a mixture comprising Auramine O, sodium hydroxide, and/or trisodium citrate in aqueous 23% ethanol. In some embodiments, the mixture may comprise approximately 0.33 mg/mL Auramine O, 13.3 mg/mL sodium hydroxide, and/or 9.67 mg/mL trisodium citrate in an aqueous 23% ethanol. Although embodiments of the present invention provide for these volumes of sputum sample, staining compound, and reagent compound, one skilled in the art may appreciate that these volumes may vary so long as the ratios of the sputum sample, the liquefaction component of the staining compound, and the staining component of the staining compound, such as Auramine O, remains at 2:2:1 respectively. Accordingly, some embodiments provide a pipette configured to acquire a sample and subsequently stain and/or liquefy the sample for processing. In other embodiments, such as shown in FIG. 9, the sachet 310 may be constructed of and/or surrounded by a polyvinyl chloride (PVC), low density polyethylene (LDPE) material, a polytetrafluoroethylene (PTFE) tape, and/or any other material suitable for limiting or eliminating off-gas generation, such as materials for insulating aluminum from the liquid after expulsion of the sachet contents.

One advantageous embodiment of the present invention includes an efficient method for detecting the presence of acid fast bacilli. Specifically, some embodiments may provide an efficient manner for digesting and/or liquefying a sputum sample and fluorescently staining the sample for detecting the presence of an acid fast bacilli. In addition, some embodiments of the present invention provide for the staining of a sputum sample without the need for heating or rinsing the sample. As discussed above in connection with staining and liquefying the sputum sample, no heating is required to fix the sample following the staining and liquefying of the sample. Rinsing may also be eliminated when excess DQ is removed as discussed in further detail below. Mycobacterial cells, such as acid-fast bacilli, are entrapped in the mucus of a sputum sample and are difficult to detect in unprocessed sputum samples. Accordingly, some embodiments include a staining compound configured to liquefy the sputum sample causing the release of microorganisms, such as acid-fast bacilli, from the entrapment in the mucus. Further, the staining compound may be configured to concurrently stain a mycobacterial cell, such as an acid-fast *bacillus*, while causing the liquefaction of the sputum sample. Thus, the viscosity of the sample may be sufficiently reduced to facilitate spreading of the sample for analysis. Moreover, ethanol is thought to aid in incorporating the fluorescent dye into the mycolic acid cell wall structure by permeabilizing the cell wall. Thus, the addition of ethanol in the solution may advantageously enhance the fluorescence seen over the typical Auramine O staining. Additionally, the added ethanol may be configured to advantageously act as a fixative for the staining compound over traditionally used agents, such as isopropyl alcohol, which may not provide for a correctly prepared specimen. The amount of ethanol added, however, may affect the sample dramatically. The addition of excess ethanol to the sample may actually hinder the dispersion and instead cause cellular aggregation. However, with the proper amount of ethanol, the dilution with ethanol has been shown to aid in sample dispersion as well as microorganism dispersion within the sample, as demonstrated by better cellular distribution on the slide.

In an alternative embodiment, a glass vial may be used rather than a pipette sachet 310 wherein the user is able to break the glass vial to release the reagent. In another alternative embodiment, the Auramine O stain may be contained in the pipette sachet 310 with the ethanol while the sodium hydroxide alone is dehydrated within the sampling chamber 300. Thus, the pipette 200 may include different reagents and methods for containing such reagents in order to effectuate proper preparation of the sample for imaging.

Moreover, although the pipette 210 may be different sizes and configurations according to embodiments described herein, the pipette may be in one embodiment about 85 to 100 mm in length, with the sampling chamber 300 about 35 to 50 mm in length, the shaft 320 about 30 to 50 mm in length, and the inlet 330 about 3-10 mm in length. In one example, the diameter of the sampling chamber 300 is larger than the diameters of the shaft 320 and inlet 330, while the shaft diameter is larger than the inlet diameter. Accordingly, embodiments described herein may advantageously provide for the sampling of a specimen as the differently sized diameters of portions of the pipette may prevent a viscous specimen from becoming stuck within the pipette. In general the pipette 210 may have a circular cross section, although it is understood that different cross sections may be employed in alternative embodiments.

According to a particularly advantageous aspect of some embodiments of the present invention, the cartridge assembly 110 may include an imaging cartridge 210 further including an imaging chamber 410. According to some embodiments, the imaging cartridge may further include a pipette dock 400 defining an opening 405 for receiving a pipette 200 therethrough. In some embodiments, the imaging cartridge may further include a cartridge blister chamber 420 containing a decolorizer-quencher (DQ) reagent therein. The cartridge blister chamber 420 may be configured to be frangible upon the application of a force to the cartridge blister chamber 420 such that the DQ reagent may enter the imaging chamber 410 in an instance in which the cartridge blister chamber 420 is broken. In some embodiments, the imaging cartridge may include additional rupture features configured to assist in the breakage of a cartridge blister disposed within the cartridge blister chamber 420. The additional rupture features may be integrally molded and/or coupled with the cartridge blister chamber in some embodiments. Additionally and/or alternatively, the imaging cartridge 210 may further include a fluid trap 430, such as a wicking chamber, configured to remove excess DQ reagent from the imaging chamber 410. In some embodiments, the imaging cartridge 210 may further include at least one footing 212, as shown in FIG. 6C. As such, when the imaging cartridge 210 is placed on a surface, such as a flat surface (e.g., a workbench), the at least one footing 212 is configured to prevent the bottom surface of the imaging cartridge 210 from contacting the surface. Accordingly, the imaging cartridge 210 may include at least one footing 212 that advantageously provides for protecting the surface of the imaging cartridge 210 from the accumulation of imaging artifacts (e.g., dirt, dust, etc.), and/or from damage (e.g., scratching, cracking, etc.).

According to some embodiments, the imaging cartridge 210 may include a baseplate 500, as shown in FIGS. 5A, 5B, 10, and 11. According to some embodiments, the baseplate 500 of the imaging cartridge 210 may be configured to exhibit hydrophilic properties. As such, the baseplate 500 may comprise a hydrophilic material and/or may be treated to exhibit hydrophilic properties. In some embodiments, the baseplate 500 of the imaging cartridge 210 may be treated such that the baseplate 500 exhibits hydrophilic properties. According to some embodiments, the baseplate 500 may comprise a treated polymethyl methacrylate material that is configured to be hydrophilic. Additionally and/or alternatively, the baseplate 500 may comprise a cyclic olefin polymer, a polystyrene, and/or a polycarbonate material. According to some embodiments, the baseplate 500 may comprise any optically suitable plastic that may be configured to exhibit hydrophilic properties. In some embodiments, it may be advantageous to only have the channels hydrophilic, while the top surfaces are slightly hydrophobic, for example exhibiting contact angles in the approximate 40° to 50° range.

In some embodiments, the baseplate 500 may define at least a portion of the imaging chamber 410. The material of the baseplate 500 may be hydrophilic such that at least a portion of the imaging chamber 410 may also be configured to exhibit hydrophilic tendencies. According to some embodiments, the portion of the imaging chamber 410 formed in the baseplate 500 may be treated with a material, compound, and/or the like so as to reduce the hydrophobicity of the portion of the imaging chamber 410 formed in the baseplate 500. In some embodiments, the treatment of the portion of the imaging chamber 410 formed in the baseplate 500 may provide improved wettability and/or enhanced smearing of the stained and/or processed sample. Additionally and/or alternatively, the treatment of the portion of the imaging chamber 410 formed in the baseplate 500 may also minimize unfavorable interaction between the material of the base plate, such as polymethyl methacrylate, and the sample, such as a viscous sputum, which may cause the detection of undesirable image artifacts. Some exemplary treatments may include oxygen plasma treatment, plasma graft polymerization of various monomers, such as ethylene oxide or hexamethyldisiloxane, adsorbtion of surfactants, adsorbtion of block copolymers, and/or the like. Another exemplary treatment of the portion of the imaging chamber 410 of the baseplate 500 may include utilizing wet chemistry polymerization methods to graft polymers thereto. In some embodiments, the surface treatment may include providing a coating of polyethylene oxide and/or silica by plasma polymerizing an ethylene oxide monomer and/or a mixture of hexamethyldisiloxane and oxygen to the portion of the imaging chamber 410 of the baseplate 500.

Figure 10:
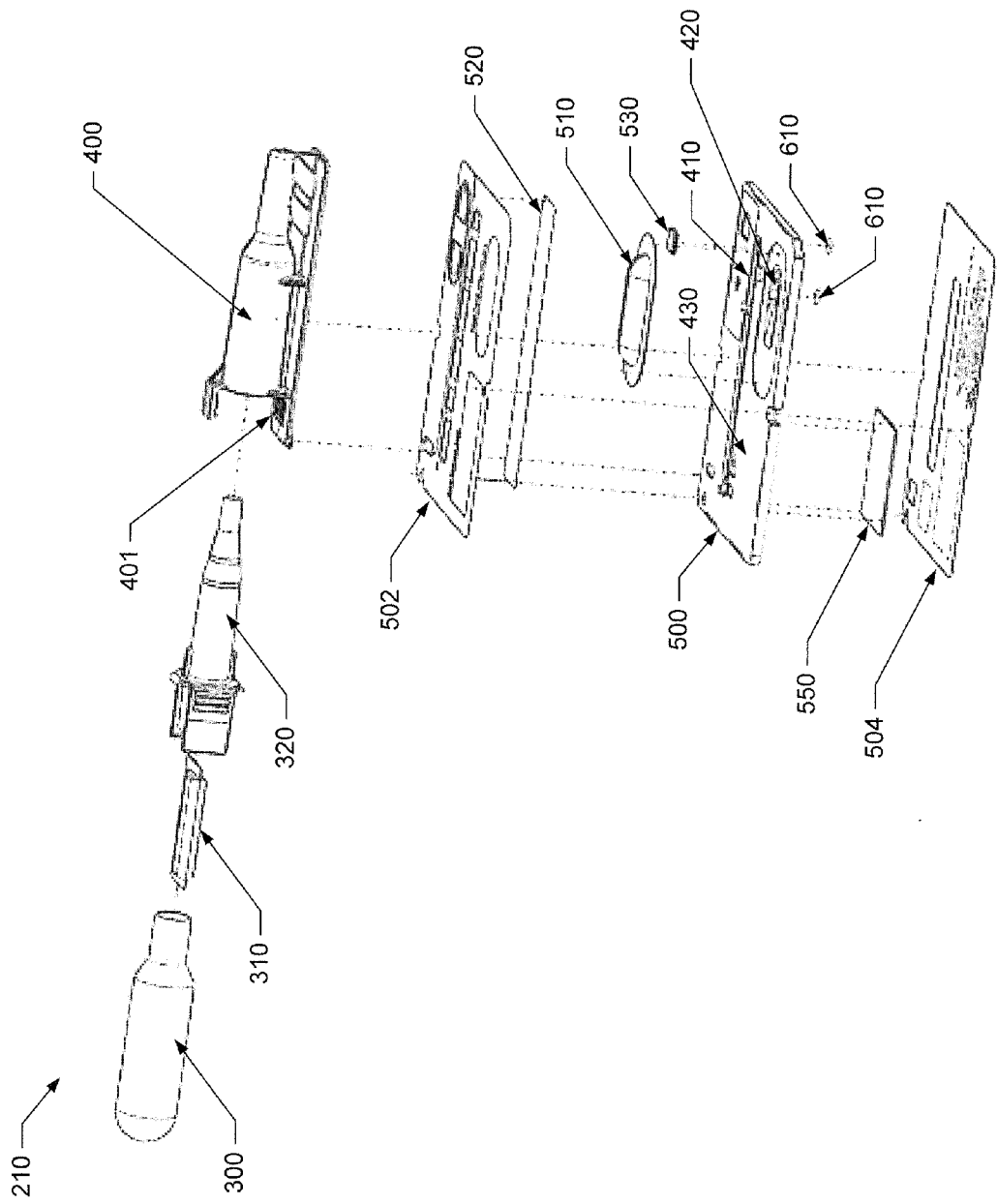
FIG. 10 illustrates an exploded view of the imaging cartridge and pipette according to other embodiments of the present invention.
Figure 11:
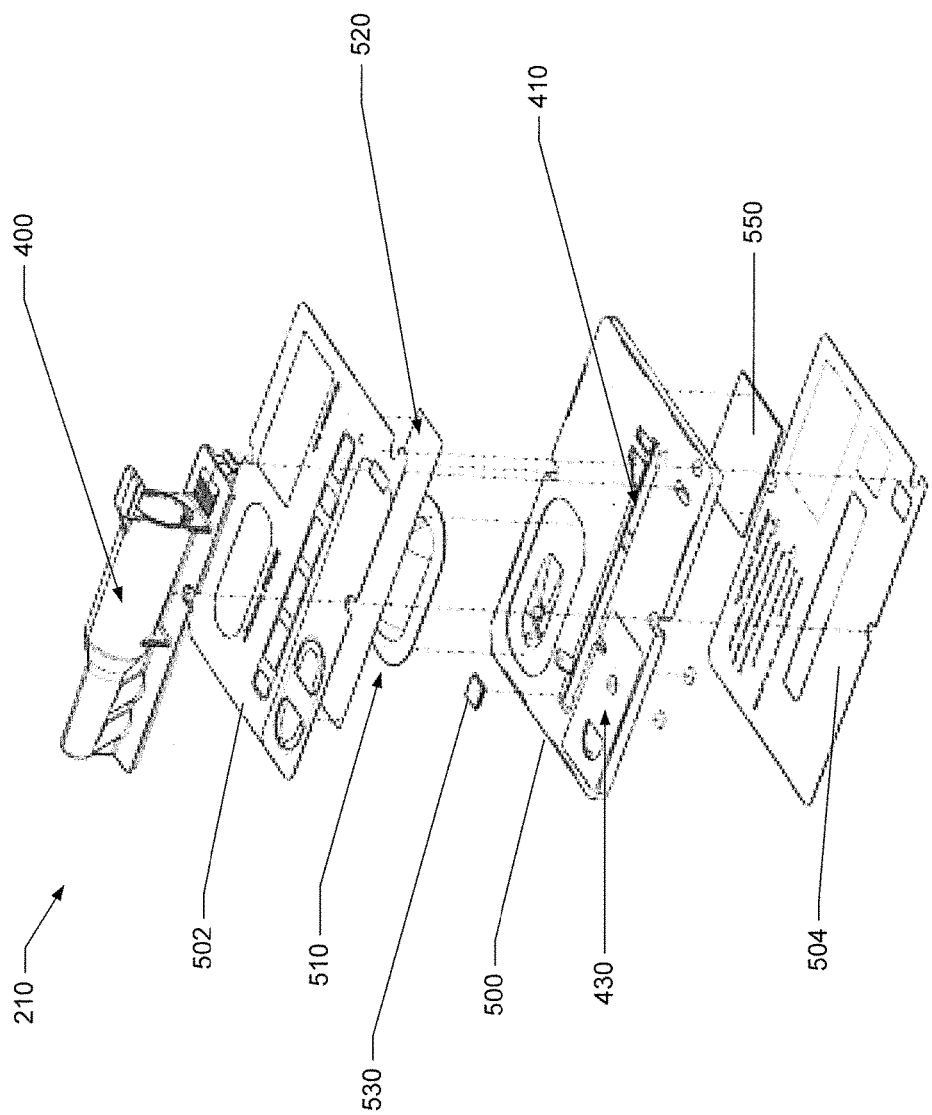
FIG. 11 illustrates an exploded view of the imaging cartridge according to other embodiments of the present invention.

According to some embodiments, an imaging chamber 410 may be covered with an imaging chamber cover 520, as shown in FIGS. 5B, 10, and 11. The imaging chamber cover 520 may comprise a porous material configured to allow a sample within the imaging chamber 410 to dry while preventing a microorganism (e.g., *mycobacterium*) or other bio-contaminant from passing through the imaging chamber cover 520 thereby maintaining bio-containment of the imaging cartridge 210. As such, the imaging chamber cover 520 may be configured to assist in containing the biological sample within the imaging cartridge 210. In some embodiments, the imaging chamber cover 520 may be constructed from a hydrophobic polycarbonate membrane having pores approximately 0.4 µm in size. Although embodiments of the present invention describe an imaging chamber cover 520 being constructed from a hydrophobic polycarbonate material, one of ordinary skill in the art may appreciate that an imaging chamber cover 520 may be constructed from any material configured to tolerate the DQ reagent, which may include ethanol. According to some embodiments, the imaging chamber cover 520 may be configured to exhibit hydrophobic properties. Additionally and/or alternatively, the imaging chamber cover 520 may comprise a material, such as a hydrophobic polycarbonate material, configured to tolerate a high pH and a high quantity of salt of a treated sputum sample, and then subsequently tolerate a low pH and the ethanol of the DQ reagent, all while impeding fluids from passing through the pores of the imaging chamber cover. According to some embodiments, the imaging chamber cover 520 may be configured to have a minimal background autofluorescence when dry. In some embodiments, the imaging chamber cover 520 may be stained black or any other non-fluorescing or non-reflecting color.

In some embodiments, the imaging cartridge 210 may also include a magnet 530 configured to spread or smear the sample within the imaging chamber 410. For example, the magnet 530, such as any material configured to be attracted or repelled by a magnetic force, may be disposed within the imaging chamber 410, which may be shaped as a longitudinal channel within the baseplate 500. In addition, the imaging chamber 410 may include a plurality of rails disposed within the imaging chamber 410, wherein the rails are configured to support the magnet 530 thereon. The rails may be shaped so as to extend fully from one end of the imaging chamber 410 to the opposite end. In some embodiments, the plurality of rails may be approximately 0.1 mm in height and approximately 0.5 mm in width. According to one embodiment, the longitudinally shaped imaging chamber 410 may be approximately 1 mm in height and approximately 65 mm in length. Further, the imaging chamber 410 may be approximately 4 mm in width at the base of the channels at the rails and approximately between 5 and 5.2 mm in width at a position above the rails. Accordingly, the magnet 530 may be configured to move freely within the imaging chamber 410 while being supported in part by the rails located therein. In some embodiments, the magnet 530 may have dimensions of approximately 5 mm×5 mm×0.9 mm. However, the magnet 530 may be configured to have any desired dimension so as to smear the sample within the imaging chamber 410 and not interfere with the imaging chamber 410 and/or imaging chamber cover 520.

According to some embodiments, the magnet 530 may be configured to move within the imaging chamber 410. For example, the magnet 530 may be configured to move from one end of the imaging chamber 410 to the opposite end of the imaging chamber 410. In particular, a magnet external to the imaging chamber may be configured to the move the magnet 530 from one end to the opposite end of the imaging chamber 410. A user may move the imaging chamber over the external magnet. In another embodiment, a user may move the external magnet over the imaging chamber. Accordingly, the external magnet may provide a magnetic force that attracts the magnet 530 within the imaging chamber 410. As the external magnet provides a magnetic force attracting the magnet 530 within the imaging chamber 410, a user may move the imaging cartridge 210 in a back and forth motion over the external magnet in one embodiment. As such, the magnet 530 within the imaging chamber 410 remains in a stationary position relative to the external magnet as the external magnet provides a magnetically attractive force while the user moves the imaging cartridge 210 back and forth with respect to the external magnet. Accordingly, the magnet 530 may be configured to move from one end of the imaging chamber 410 to the opposite end of the imaging chamber 410 by moving the imaging cartridge 210 over the external magnet. It is understood that other mechanisms can be utilized to spread the sample within the imaging chamber 410 according to additional embodiments. For example, non-magnetic elements, such as ball bearings, could be used to spread the sample by tilting the imaging cartridge 210 where the mass of the element is greater than the viscosity of the sample. Other actuators could be utilized for metering, such as magnetically-driven actuators or valves, for spreading the sample.

Figure 6A:
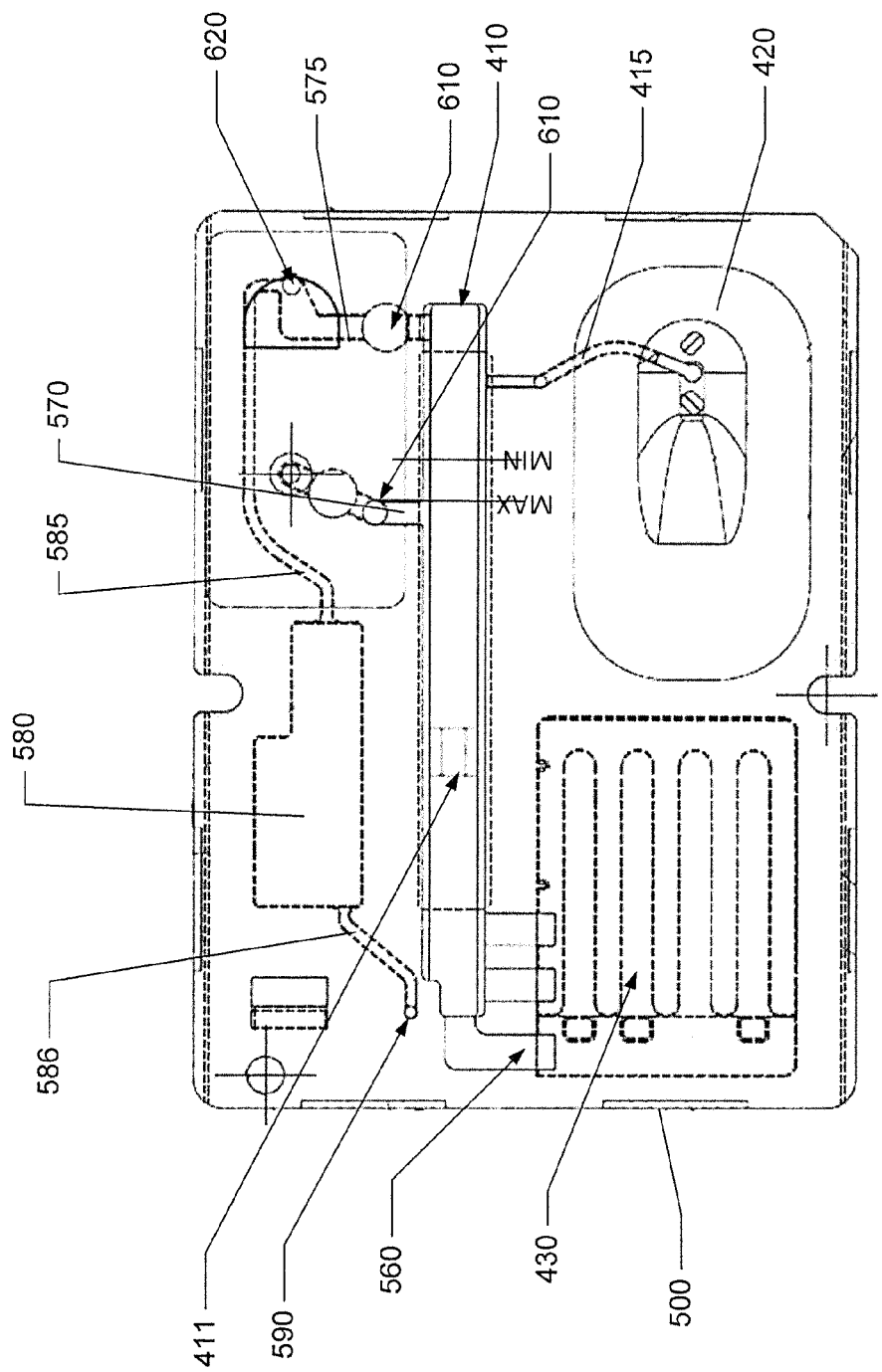
FIG. 6A illustrates a baseplate of an imaging cartridge according to some embodiments of the present invention.
Figure 12:
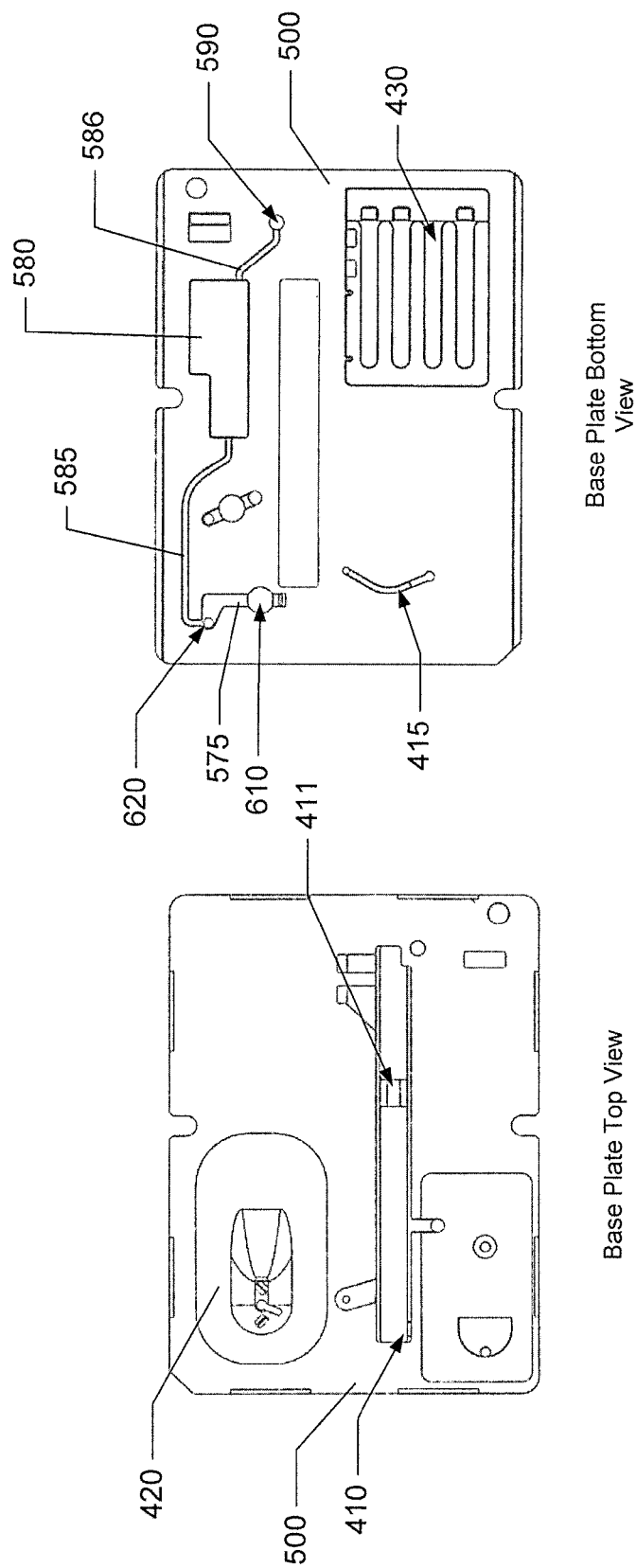
FIG. 12 illustrates top and bottom views of a baseplate of an imaging cartridge according to other embodiments of the present invention.

According to some embodiments, the imaging cartridge 210 may further include a process control feature, such as a process control well 411, as shown in FIGS. 6A and 12. In some embodiments, the imaging chamber 410 may define the process control well 411. For example, a process control well 411 may be defined by a shallow well defined along the length of the imaging chamber 410. According to some embodiments, the process control well 411 may be configured to indicate when a specimen sample has been properly prepared and is ready for analysis. For example, the process control well 411 may include approximately 3 µL of a silicone adhesive. In some embodiments, the process control well 411 may include a material configured to stain upon exposure to a properly stained specimen sample. As previously mentioned, a magnet 530 may be used to spread or smear the sample within the imaging chamber 410. As such, when a magnet spreads a properly prepared specimen sample within the imaging chamber 410, the process control well 411 may be exposed to the properly prepared sample as the magnet moves from a first end to an opposite end of the imaging chamber 410. According to some embodiments, a sample that has been stained properly will impart the stain onto the silicone adhesive disposed within the process control well 411. If the sample has been improperly prepared, the process control feature may be configured to indicate the sample has not been prepared correctly. For example, when a sample has been improperly prepared, the silicone adhesive disposed within the process control well 411 may be configured to not receive or take up a stain. In another embodiment, when a sample has been improperly prepared, the silicone adhesive disposed within the process control well 411 may be configured to decolorize if the specimen sample was not properly prepared. As such, the process control well 411 may provide for a process control feature configured to produce a brighter, stained spot on a darker background, thus indicating the specimen was stained, subjected to the DQ reagent, properly prepared, and/or ready for further analysis.

In some embodiments, the imaging cartridge 210 may further include a baseplate 500, which may define at least a portion of a cartridge blister chamber 420. In some embodiments, the cartridge blister chamber 420 may be defined by at least a portion of the baseplate 500, a cartridge blister 510 and/or a combination thereof. According to some embodiments, the cartridge blister 510 may include a DQ reagent. In some embodiments, the cartridge blister 510 may be configured to release the DQ reagent into the imaging chamber 410. For example, the cartridge blister 510 may be a frangible blister, wherein a portion of the cartridge blister is configured to break upon the application of a force applied thereto. In some embodiments, the cartridge blister chamber 420 may include at least one rupture feature configured to aid in the breaking of the cartridge blister. Upon the cartridge blister 510 breaking, fluid communication between the cartridge blister chamber 420 and the imaging camber 410 is achieved. For example, a decolorizer-quencher channel 415 may provide a channel for fluid communication between a cartridge blister chamber 420 and the imaging chamber 410. As such, a user may apply a force to the cartridge blister 510 causing the cartridge blister 510 to burst and release the DQ reagent into the imaging chamber 410. In some embodiments, the DQ reagent may comprise at least one of hydrochloric acid, Evans blue dye, ethanol, and/or glycerol. In other embodiments, such as shown in FIG. 12, various features (such as, for example, the decolorizer-quencher channel 415) may have different configurations.

Figure 6B:
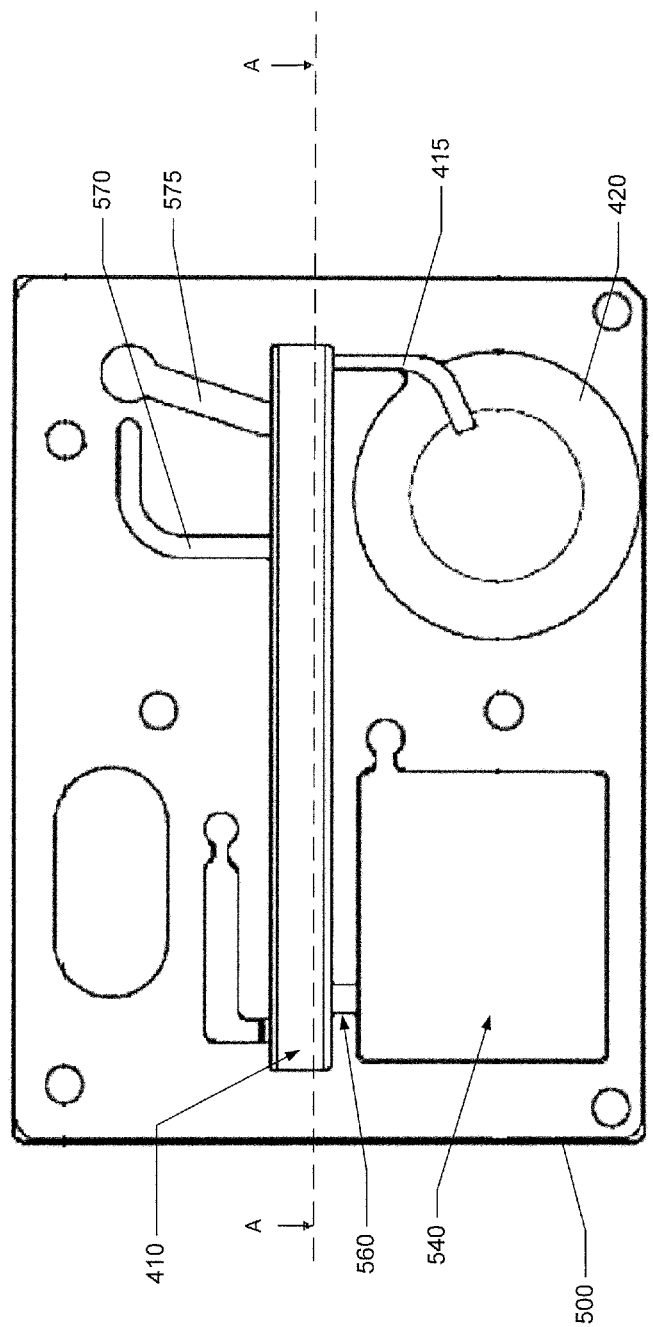
FIG. 6B illustrates a baseplate of an imaging cartridge according to some embodiments of the present invention.
Figure 6C:
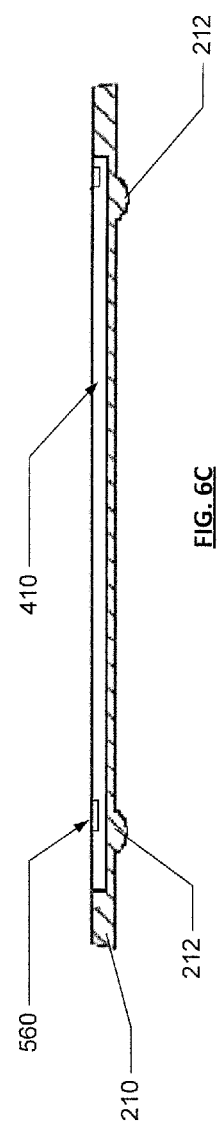
FIG. 6C illustrates a cross-sectional view of the baseplate of an imaging cartridge shown in FIG. 6B along the line A-A according to some embodiments of the present invention.

Additionally and/or alternatively, the imaging cartridge 210 may include a baseplate 500 that defines at least part of a fluid trap 430, such as a wicking chamber. In some embodiments, the fluid trap 430 may further comprise a wicking pad 550 configured to absorb excess DQ reagent from the imaging chamber 410. As such, the imaging chamber 410 may be in fluid communication with the fluid trap 430. According to some embodiments, the fluid trap 430 may comprise a fluid trap inlet 560 disposed between the imaging chamber 410 and the fluid trap 430, as shown in FIG. 6A. In other embodiments, such as shown in FIG. 12, there is no fluid trap inlet 560. In some embodiments, the fluid trap inlet 560 may be configured to allow passage of excess DQ reagent when the imaging cartridge 210 is oriented in a particular manner, as shown in FIGS. 6B and 6C. For example, as shown in FIG. 6C, the fluid trap inlet 560 may be positioned such that only a portion of the depth of the imaging chamber 410 is in communication with the fluid trap inlet 560. Specifically, FIG. 6C illustrates a cross-sectional view of FIG. 6B taken along line A-A and towards the bottom half of the imaging cartridge below line A-A. The fluid trap inlet 560 may be positioned towards the top half of the imaging chamber 410 such that the entrance of the fluid trap inlet 560 is in fluid communication with the top half of the imaging chamber 410. As such, the DQ reagent may flow into the imaging chamber 410 and remain on the smeared sputum sample until a user inverts the imaging cartridge 210 and/or tips the imaging cartridge 210 such that the excess DQ reagent flows above the bottom portion of the imaging chamber 410 and into the fluid trap 430 via the fluid trap inlet 560 disposed approximate to the upper portion of the imaging chamber 410. In one embodiment, the imaging chamber 410 may have a depth of approximately 1 mm, and the fluid trap inlet 560 is in fluid communication with approximately the top 0.5 mm of the imaging chamber 410. In an alternative embodiment, a passive wicking mechanism could be used. For example, a passive wicking pump may be implemented that allows the DQ to be slowly wicked away by mechanically controlling the flow rate of wicking, thereby eliminating the need to invert the imaging cartridge as well as a timed step in the process.

Figure 5A:
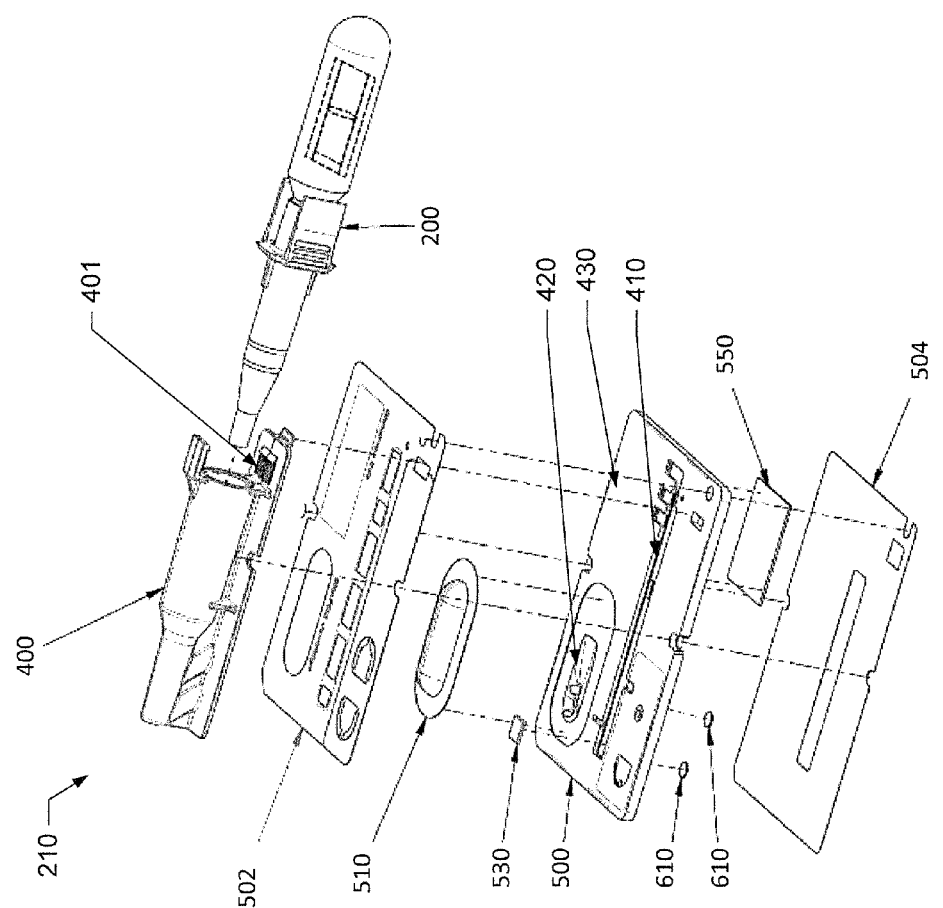
FIG. 5A illustrates an exploded view of the imaging cartridge and pipette according to some embodiments of the present invention.
Figure 5C:
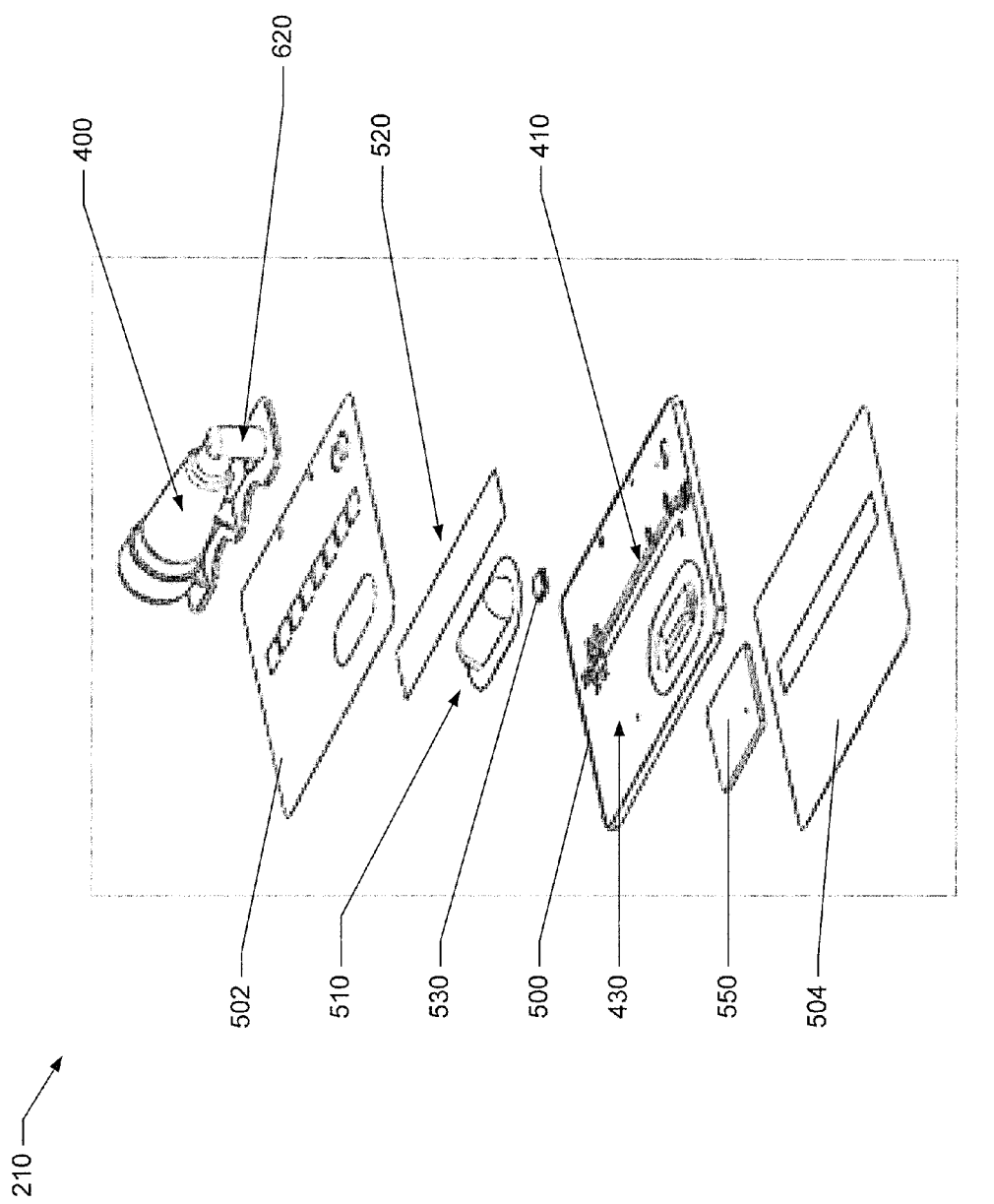
FIG. 5C illustrates an exploded view of the imaging cartridge according to some embodiments of the present invention.

According to some embodiments, the imaging cartridge 210 may further include at least one vent 590 in fluid communication with an overflow chamber 580 and venting channels 585, 586 defined in the baseplate 500. Specifically, the vent 590 may be configured to allow excess gases to be released from the cartridge assembly 210. For example, during the processing of the sputum sample within the pipette 200 and/or imaging cartridge 210, the pressure within the pipette 200 and/or imaging cartridge 210 may increase from the production of a gaseous substance, such as hydrogen gas. The production of a gaseous substance may result in providing motive force for unmetered specimen into the imaging chamber. As such, the venting channels 585, 586 and overflow chamber 580 may accommodate for the build-up of gaseous by-products, while the vent 590 may provide for the release of excess gaseous by-products and/or pressure created during the processing of the sputum sample. The vent 590 may be disposed below the cover 520 such that the release of any biological agents through the vent and cover is prevented. In some embodiments, the imaging cartridge 210 may be configured to prevent, impede, and/or prohibit the release of any biological agents and/or prohibit the loss of fluid seals configured to retain the specimen sample within the imaging cartridge even if the vent 590 is blocked and excess gaseous by-products and/or pressure is created within the imaging cartridge. According to one embodiment, the imaging chamber 410 may be in fluid communication with the pipette dock 400, the cartridge blister chamber 420, and/or the fluid trap 430. In other embodiments, such as shown in FIG. 12, the vent 590 may have a different configuration. According to some embodiments, the imaging cartridge 210 may further include at least one valve 620 configured to allow for the sample to flow from the pipette 200 to the imaging chamber 410 of the imaging cartridge 210. In some embodiments, the pipette dock 400 and the imaging chamber 410 may be in fluid communication with one another, and the imaging cartridge may include a valve 620 disposed in the fluid flow path between the imaging chamber 410 and the pipette dock 400, as shown in FIGS. 5A and 10. As shown in FIG. 6A, an inlet channel 575 is defined in the baseplate 500. A valve 620 may be disposed between the pipette inlet 330 and the inlet channel 575. In one embodiment, the valve 620 may be integrated into the pipette dock 400, as shown in FIG. 5C. In some embodiments, the imaging cartridge 210 may include at least one valve 620 configured to allow for the sample to flow from the pipette 200 to the imaging chamber 410 via an inlet channel 575 and further configured to allow for a portion of the sample to flow from the imaging chamber 410 back to the pipette 200 via a return channel 570. As such, the imaging cartridge 210 may be configured to provide for, with at least the pipette 200, the self-metering of a specimen sample for analysis. According to one embodiment, the imaging cartridge 210 may include at least one valve 620 configured to allow for the sample to flow from the pipette 200 to the imaging chamber 410 while preventing the sample from flowing back into the pipette 200 when an appropriate amount of specimen sample is metered from a pipette having graduated marks. It is understood that various types of valves 620 may be employed to meter a specimen from the pipette into the imaging chamber and further, it is understood that various types of valves 620 may provide for different desired functionality, such as providing for the self-metering of a specimen sample, and/or for preventing back flow of a specimen. Some example valves 620 may include a three-way valve, a one-way check valve, a double check valve, a duckbill valve and/or a swellable disk valve. In some embodiments, the swellable disk valve may comprise a material including polyacrylamide.

Figure 7:
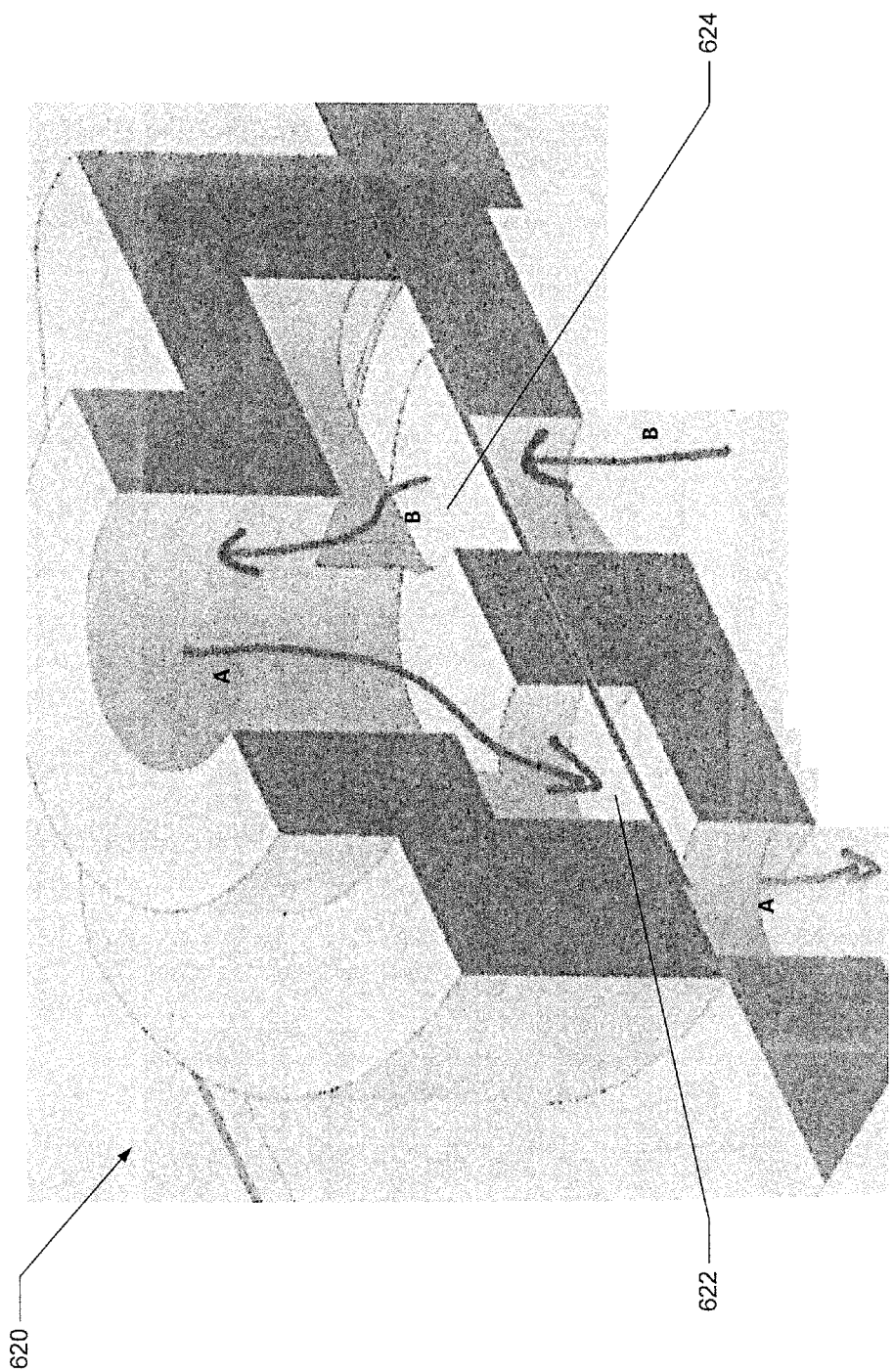
FIG. 7 illustrates a valve of the imaging cartridge according to some embodiments of the present invention.

For example, as shown in FIG. 7, a metering valve 620, such as a double check valve assembly, may be configured to allow the sputum sample to flow from the pipette 200 to the imaging chamber 410 when the pipette 200 is depressed along the flowpath A. Likewise, when the pipette 200 is released, the inlet flap valve may be configured to allow only air to return into the pipette 200 along the flowpath B and prohibit the sputum sample located within the imaging chamber 410 from returning to the pipette 200. For example, the double check valve assembly may be configured to have at least two flaps. A first flap 622 may be configured to open along the flowpath A only when a positive pressure is applied thereto. In addition, the first flap 622 may be configured to close when a negative pressure is applied thereto. Further, a second flap 624 may be configured to open along flowpath B only when a negative pressure is applied thereto. The second flap 624 may be further configured to close when a positive pressure is applied thereto. Thus, the double check valve assembly is configured to allow the passage of fluid from the pipette 200 to the imaging chamber 410 when the pipette sampling chamber 300 is depressed or otherwise actuated.

In addition, embodiments may advantageously provide for the self-metering of a sputum sample from the pipette sampling chamber 300 to the imaging chamber 410. In some embodiments, the metering valve 620 may provide for an amount of sputum sample to be transferred from the pipette 200 to the imaging chamber 410 such that the amount of the sputum sample provided within the imaging chamber is approximately an amount corresponding to the max fill volume, as shown in FIG. 6A. Accordingly, embodiments may advantageously provide for a self-metering imaging cartridge configured to meter an appropriate amount of a sample without requiring an exact measurement. In some embodiments, when a pipette 200 configured to be coupled with the pipette dock 400 is coupled to the pipette dock, an amount of sputum sample may be transferred from the pipette sampling chamber 300 to the imaging cartridge 210 without requiring an exact measurement. As shown in FIG. 6A, a baseplate 500 configured to provide for the self-metering of a sample after the sample has been obtained via the pipette 200 may include a return channel 570 with an swellable insert 610 located therein. In some embodiments, the return channel 570 may correspond with a max fill volume of a sample within the imaging chamber 410. According to some embodiments, the pipette 200 may be depressed allowing an amount of the sample to flow from the pipette into the imaging cartridge 210 via an inlet channel 575. According to some embodiments, when the sputum sample travels from the pipette 200 to the imaging chamber 410, the inserts 610 within the inlet channel 575 and return channel 570 become wetted. According to some embodiments, when the inserts 610 are wetted, the inserts increase in size. In some embodiments, the inserts 610 may be configured, in conjunction with the valve 620 to allow for an amount of sputum sample to be transferred from the pipette 200 to the imaging chamber 410 that is approximately between the minimum and maximum amounts defined by demarcations, lines, or other indicia on the baseplate 500. In other embodiments, such as shown in FIG. 12, there are no minimum or maximum demarcations. According to another embodiment, the inserts 610 may be configured, in conjunction with the metering valve 620 to allow for an amount of sputum sample to be transferred from the pipette 200 to the imaging chamber 410 that is approximately between the minimum and maximum amounts that may be defined by location of an inlet channel 575 and a return channel 570. In some embodiments, the pipette sampling chamber 300 may be depressed causing the sputum sample to travel from the pipette 200 to the imaging chamber 410. As such, the insert 610 disposed within the inlet channel 575 may begin to expand. When the amount of sample transferred between the pipette 200 to the imaging chamber 410 is greater than a maximum amount, the insert 610 disposed within the return channel 570 may be configured to expand as the excess sputum travels through the return channel 570. Accordingly, the metering valve 620 may be configured to remove the excess amount of sample disposed within the imaging chamber 410, and may be further configured to remove the excess amount of the sputum sample from the imaging chamber 410 back to the pipette 200. For example, the metering valve 620 may be configured to allow for the passage of fluid from the pipette 200 to the imaging chamber 410 via the first flap 622 when the pipette sampling chamber 300 is depressed, and allow for the return of a fluid from a return channel 570 via the second flap 624 when the pipette sampling chamber 300 is released. As such, embodiments presented herein may advantageously provide for the self-metering of a sputum sample within the imaging cartridge 210 for analysis after an amount of sputum sample has been acquired by a pipette 200 by providing a circular flow of fluid, sample, and/or other specimen disposed within the pipette 200 through an inlet channel 570, the imaging chamber 410, and the return channel 575.

In an alternative embodiment, the imaging cartridge 210 may include a duckbill metering valve 625, as shown in FIG. 5B. The duckbill metering valve 625 may be configured to open and provide for a fluid passageway between the pipette 200 and the imaging cartridge 410. Specifically, when the pipette sampling chamber 300 is depressed, the increase in pressure applied towards the duckbill metering valve 625 may cause the duckbill metering valve 625 to open. When the pressure applied to the duckbill metering valve 625 returns below a predefined level, the duckbill metering valve 625 may be configured to close. In some embodiments, the return channel 575 may bypass the duckbill metering valve 625 such that the sample may return to the pipette 200 when the pipette sampling chamber 300 is released.

In some embodiments, the imaging cartridge 210 may include inserts 610 configured to block inlet channel 575 and a return channel 570 fluidly connected to the imaging chamber 410. For example, the inserts 610 may be inserted into the inlet channel 575 and return channel 570, which are fluidly connected to the imaging chamber 410 such that when the inserts 610 are wetted with a fluid, sample, and/or other liquid, the inserts 610 expand thereby blocking the channels from allowing additional liquids to pass. According to some embodiments, the inserts 610 may comprise polyacrylamide crystals configured to be water-swellable such that the inserts 610 absorb fluids slowly enough to allow the proper amount of sample to pass through the inlet channel to the imaging chamber 410, but expand after a period of time to block the inlet and/or outlet channels after the desired amount of sample has been transferred, metered, or otherwise provided to the imaging chamber 410. In another embodiment, the inserts 610 may comprise at least a polyacrylamide material.

According to some embodiments, the inserts 610 may comprise a porous material that expands when wetted with a fluid, sample, and/or other liquid. Additionally and/or alternatively, the inserts may comprise a porous material configured to significantly reduce the porosity of the material when wetted with a fluid, sample, and/or other liquid. In some embodiments, the inserts 610 may be porous to allow for fluid to flow there through initially and subsequently, after being wetted with a fluid, sample, and/or other liquid passing there through, be configured to prohibit the flow of the fluid, sample, and/or other liquid after the porosity of the material has been reduced and/or eliminated.

Figure 8:
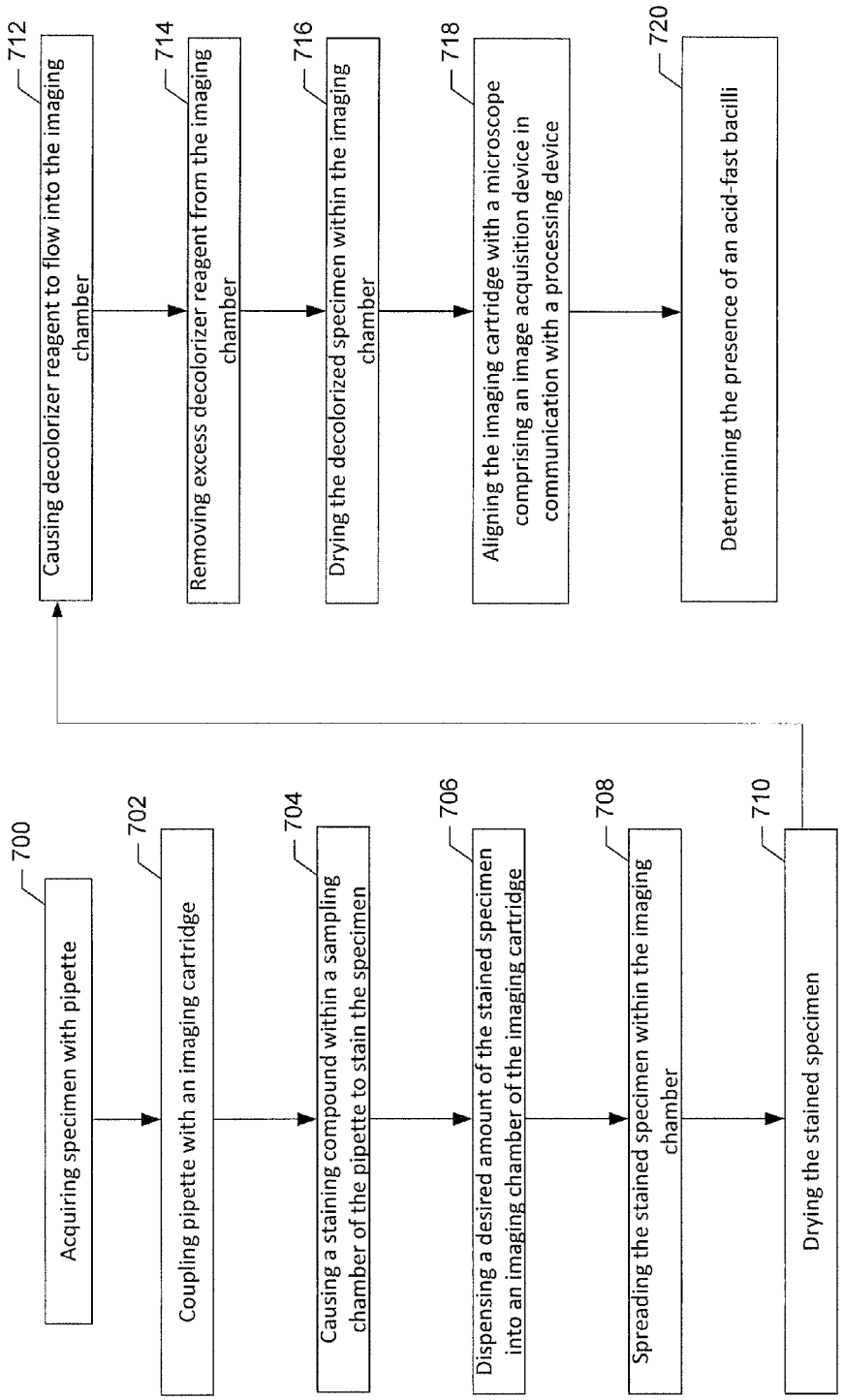
FIG. 8 illustrates a flowchart detailing a method for detecting a specimen within a sample according to some embodiments of the present invention.

According to a particularly advantageous aspect of some embodiments of the present invention, a method for detecting a microorganism, such as acid-fast bacilli, with sputum smear microscopy is provided, as shown in FIG. 8. Some embodiments provide for the detection of acid-fast bacilli, such as *Mycobacterium tuberculosis*. According to one embodiment, a user may acquire a specimen for testing using a pipette 200. See Block 700. The user may obtain the desired amount of sputum sample with a pipette 200 by inserting the pipette inlet 330 into a sample container, drawing the sample into the pipette 200 via the pipette inlet 330, and by metering the sample using the graduation marks disposed along the pipette shaft 320. According to some embodiments, the user may aspirate approximately 0.2 mL of the sputum sample into the pipette 200.

Once the user has obtained the desired amount of specimen within the pipette 200, the user may dock the pipette 200 to the imaging cartridge 210 via the opening 405 of the pipette dock 400. See Block 702. In some embodiments, the user may dock the pipette 200 to the imaging cartridge 210 via the opening 405 of the pipette dock 400 such that the pipette 200 is irreversibly coupled to the imaging cartridge.

Once the pipette 200 has been secured to the pipette dock 400, a user may then cause the pipette sachet 310 to burst within the sampling chamber 300 causing a staining compound to stain the sputum sample. See Block 704. The pipette sachet 310 may be configured to burst upon the application of a force thereto. In some embodiments, the pipette sachet 310 may include a reagent configured to rehydrate and/or re-dissolve a staining compound disposed on an interior surface of the sampling chamber 300. Once the user breaks the pipette sachet 310 to release the solvent reagent into the sampling chamber 300, the user may shake the imaging cartridge 210 to initiate the staining and/or liquefaction of the sputum sample disposed within the pipette 200. After shaking the imaging cartridge 210 to initiate the mixing, staining, and liquefaction of the sputum sample disposed within the pipette 200, which is coupled with the imaging cartridge 210, the user may then wait for a period of time to ensure the sample has been properly stained. In some embodiments, the user may wait for up to about fifteen minutes. In another embodiment, the user may wait for up to about five minutes. According to yet another embodiment, the user may wait for up to about two minutes. While the user waits to ensure for proper staining, the user may optionally shake the imaging cartridge as desired.

After the sputum sample has been properly stained and processed, the user may then optionally orient the imaging cartridge 210 such that pipette 200 is disposed in a vertical fashion and the sampling chamber 300 of the pipette 200 is disposed above the pipette inlet 330. Once oriented in a vertical fashion, the user may then accurately dispense the sample from the pipette 200 into the imaging cartridge 210 in accordance with visual indicia disposed on the imaging cartridge, which may provide instruction as to an appropriate maximum and/or minimum amount of sample to be dispensed. In another embodiment, the user may accurately dispense the sample from the pipette 200 into the imaging cartridge 210, which may be configured to intrinsically meter the appropriate amount of sample from the pipette to the imaging cartridge. For example, the return channel 570 may be disposed such that excess sample is removed from the imaging cartridge 210, and the remaining amount of sample disposed within the imaging cartridge is an appropriate amount of the sample. Accordingly, the user may then dispense the stained sputum sample into the imaging cartridge by depressing the pipette sampling chamber 300. See Block 706. Depression of the pipette sampling chamber 300 may cause the activation of a valve, such as the metering valve 620, as discussed above. In some embodiments, the user may dispense the sputum sample from the pipette 200 into the imaging cartridge 210 by depressing the pipette sampling chamber 300 and receiving confirmation that an appropriate amount of the stained sample has entered into the imaging cartridge 210. According to one embodiment, the imaging cartridge 210 may include a visual indicia configured to provide the user with feedback confirming that an appropriate amount of the sputum sample is located within the imaging chamber 410 of the imaging cartridge 210. The visual indicia may include a minimum and maximum fill line located along the imaging chamber 410 of the imaging cartridge 210. According to one embodiment, the imaging cartridge 210 may further comprise a return channel 570 disposed above the maximum fill line. As such, if a user provides the imaging chamber 410 with an excess of the stained sputum sample, the excess amount will flow thorough the return channel 570 and back into the pipette. Although the metering of the sputum sample into the imaging chamber 410 may be accomplished by manually manipulating the imaging cartridge, it is understood that the metering may be carried out using an automated process thereby eliminating user intervention. For example, depressing the pipette sampling chamber 300 or actuating another mechanism could cause an exact amount of sample to be provided to the imaging chamber 410.

According to one embodiment of the present invention, a user may dispense approximately 60 μL of the stained, liquefied, and/or processed sputum sample into the imaging chamber 410 of the imaging cartridge 210. Once the user has placed the desired amount of the stained sample into the imaging chamber 410, the user may then disperse the stained sample within the imaging chamber 410 by sliding a magnet 530 back and forth within the imaging chamber 410. See Block 708. The magnet 530 may be configured to move from one end of the imaging chamber 410 to the opposite end of the imaging chamber 410. In particular, the user may take the imaging cartridge 210 and move the imaging cartridge over a stationary magnet disposed outside of the imaging cartridge 210 in a back and forth motion that is parallel to the longitudinal direction of the imaging chamber 410. Accordingly, the stationary magnet may provide a magnetic force that attracts the magnet 530 located within the imaging chamber 410 so as to bias the magnet 530 to remain stationary with respect to the outside magnet. As such, when the user moves the imaging cartridge 210 in a back and forth motion, the magnet 530 moves from one end of the imaging chamber 410 to the opposite end of the imaging chamber 410, thereby dispersing the stained sample throughout the imaging chamber 410.

Subsequently, in some embodiments, the user may then allow for the dispersed sample located within the imaging chamber 410 to dry. See Block 710. According to some embodiments, the dispersed stained sputum sample may be dried in approximately 10 minutes. In another embodiment, the dispersed stained sputum sample may be dried within the imaging chamber 410 within 30 minutes. Yet still, in another embodiment, the dispersed stained sputum sample may be dried within approximately 60 minutes. According to some embodiments, the dispersed stained sputum sample may be dried within approximately 90 minutes. The amount of time required for the dispersed stained sputum sample to dry may vary and may be dependent upon the ambient temperature, humidity, and/or other environmental factors. As such, some embodiments of the present invention may provide for additional means for drying the dispersed stained sputum sample located within the imaging chamber 410.

Once the sputum sample has dried within the imaging chamber 410, the user may provide a decolorizer-quencher (DQ) reagent to the imaging chamber 410. See Block 712. According to some embodiments, the DQ reagent may be disposed within a cartridge blister chamber 420. The cartridge blister chamber 420 may be defined by at least a portion of the baseplate 500, a cartridge blister 510, and/or a combination thereof. According to some embodiments, the cartridge blister chamber 420 may be defined by the cartridge blister 510, which may be configured to release the DQ reagent into the imaging chamber 410. The user may burst the cartridge blister 510 causing the DQ reagent to enter into the imaging chamber 410. In some embodiments, the DQ reagent may be at least 300 μL in volume. According to some embodiments the DQ reagent may be at least 450 μL in volume. In some embodiments, the DQ reagent may be approximately between 400 and 450 μL in volume. In yet another embodiment, the DQ reagent may be approximately 425 μL in volume. Accordingly, the volume of the DQ reagent is sufficient enough such that the imaging chamber 410 is substantially filled and the entire length of the imaging chamber 410 is covered with the DQ reagent.

Once the DQ reagent is released into the imaging chamber 410, the user may then wait for a period of time to allow the DQ reagent to remove the stain from the sample before removing any excess DQ reagent from the imaging chamber 410. See Block 714. According to some embodiments, the user may wait approximately 3 minutes. After which, the user may then orient the imaging cartridge 210 to remove excess DQ reagent from the imaging chamber 410. For example, a user may orient the imaging cartridge 210 such that the fluid trap 430 and the pipette sampling chamber 300 is disposed towards the bottom of the imaging cartridge 210. Accordingly, once the DQ reagent has been removed from the imaging chamber 410, the user may then wait an additional amount of time to ensure the processed sputum sample has dried within the imaging chamber 410. See Block 716. Once the sample has dried, the imaging cartridge 210 is ready for imaging and microscopy inspection. The sample may be stable for a period of time (e.g., at least about 2 hours) to facilitate batch processing of the sample.

Accordingly, the imaging cartridge 210 may be received within the system 100 to be imaged. According to some embodiments, the imaging cartridge 210 may further include alignment fiducials disposed proximate to the imaging chamber 410 such that the imaging chamber 410 is aligned with the microscope 160. See Block 718. Once the cartridge is aligned with the microscope 160 and/or image acquisition device 130, the image acquisition device 130 may be configured to take a plurality of images 135 of the processed sample. Accordingly, the computing device 120 may receive image data corresponding to the plurality of images acquired by the image acquisition device 130. According to some embodiments, the computing device 120 may be configured to analyze and determine the number of acid-fast bacilli per image so as to determine a positive or negative test result, based at least in part on the acid-fast bacilli count. See Block 720.

According to some embodiments, the imaging cartridge 200 may be assembled in a variety of manners. For example, components of the imaging cartridge may be assembled together via a pressure sensitive adhesive, via thermal and/or ultrasonic welding, and/or via a gasket. In some embodiments, for example, pressure sensitive laminates may be used in conjunction with a thermal pressing process. In one embodiment, the imaging cartridge 210 may be assembled by positioning the valves 620 and a wicking pad 550 within the baseplate 500. A bottom label 504, which may comprise a label, barcode, and/or other visual indicia for identifying the imaging cartridge 210, may be laminated to the baseplate 500. The magnet 530 and the cartridge blister 510 may then be placed within the baseplate 500. Subsequently, the imaging chamber cover 520 may be assembled with the top label 502 and laminated to the previously assembled baseplate 500 and bottom label 504. Once the top label 502 is coupled with the baseplate 500 and bottom label 504, the pipette dock 400 may be attached to the imaging cartridge 210. According to some embodiments, the imaging cartridge 210 may be assembled by coupling a baseplate 500 with a top label 502 and a bottom label 504 such that the top label and bottom label fluidly seal compartments, chambers, and/or channels within the baseplate 500.

In some embodiments, a pipette dock 400 may be coupled to the imaging cartridge 210 using an adhesive. In another embodiment, the pipette dock 400 may mate with the imaging cartridge 210 via a friction fit and/or a snap fit connection. Further still, the pipette dock 400 may be attached to the imaging cartridge 210 via ultrasonic and/or thermal welding. In another embodiment of the present invention, the bottom label 504, baseplate 500, top label 502, and/or pipette dock 400 may be coupled to one another via a thermal and/or ultrasonic welding process. By employing a thermal and/or ultrasonic welding process, adhesive materials are eliminated. Thermal and/or ultrasonic welding processes may utilize compression seals whereby multiple seal points are used to seal and assemble the aforementioned components together.

According to some embodiments, the bottom label 504 may be attached to the baseplate 500 via a pressure sensitive adhesive. Once the bottom label 504 is coupled with the baseplate 500, a gasket may be disposed between the top label 502 and the baseplate 500. In some embodiments, the gasket may comprise a thermoplastic elastomer material. In addition, the top label 502 may comprise a material similar to the baseplate 500 and may be further configured to attach to the baseplate via a friction fit and/or snap fit. Accordingly, the top label 502 and the baseplate 500 may be coupled to one another in a secure fit with a gasket disposed therebetween. The gasket may be configured to provide a fluidproof seal when the top label 502 is mechanically clamped with the baseplate 500. In addition, the gasket may include one or more inserts 610 or valves 620 integrated therein such that the inserts and valves do not need to be separately assembled.

In another embodiment, the imaging cartridge 210 may be assembled by placing a wicking pad 550 within a fluid trap 430 of a baseplate 500, as shown in FIGS. 5B and 11. According to another embodiment, the imaging cartridge 210 may be assembled by placing any suitable device configured to trap a fluid therein within the fluid trap 430 of the baseplate 500. As such, the fluid trap 430 may be configured to remove excess liquid, fluid, sample fluids, and/or decolorizer reagent from the imaging chamber 410 of the imaging cartridge 210. The baseplate 500 may further comprise a label, barcode, and/or other visual indicia for identifying the imaging cartridge 210. In addition, a magnet 530 may be placed within the imaging chamber 410 and the cartridge blister 510 may be placed within the cartridge blister chamber 420. Once the cartridge blister 510, the magnet 530, and the wicking pad 550 are inserted within the cartridge blister chamber 420, the imaging chamber 410, and the fluid trap 430 respectively, a first laminate 505 may be disposed over the assembled baseplate 500 to secure the components therein. An imaging chamber cover 520 may then be disposed over the first thermal laminate 505, and may be further secured by placing a second thermal laminate 506 thereon. Additionally and/or alternatively, the second thermal laminate 506 may be configured to secure a top cover plate 507 to form the imaging cartridge 210. In some embodiments, a duckbill metering valve 625 may be disposed between the second thermal laminate 506 and the top cover plate 507. Additionally and/or alternatively, the second thermal laminate 506 may be configured to secure the duckbill metering valve 625 to the top cover plate 507. In some embodiments, the top cover plate 507 may be coupled to a pipette dock 400 via a friction fit and/or the like. Accordingly, the top cover plate 507 may be configured to receive the pipette dock 400 and provide for the fluid communication between the pipette dock 400 and the imaging chamber 410 of the imaging cartridge 210.

Accordingly, embodiments of the present invention provide a number of advantages for determining the presence of acid-fast bacilli, such as *Mycobacterium tuberculosis*. For example, embodiments of the present invention provide a cartridge assembly for analyzing a specimen in a biologically-contained system. As such, errors in detecting the presence of a specie in a sample, such as errors due to contamination of a specimen sample, are decreased. In addition, less technical training is required for processing a sputum sample according to embodiments of the present invention. Moreover, the potential exposure to the technician to potentially hazardous bacteria is reduced. The imaging cartridge may also be formed of inexpensive and easily assembled components to allow the imaging cartridge to be disposable.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed. Although specific terms are employed herein, they are used in a generic and descriptive sense only and not for purposes of limitation.

That which is claimed:

1. An assembly for preparing a specimen for determining the presence of at least one microorganism specie in the specimen, the assembly comprising:
   a pipette configured to acquire a specimen from a sample wherein the pipette comprises an inlet, a sampling chamber, and a shaft disposed therebetween; and
   an imaging cartridge configured to couple to the pipette such that the specimen is bio-contained therein, wherein the imaging cartridge comprises:
   a pipette dock configured to at least partially receive the shaft of the pipette therein;
   an imaging chamber configured to be in fluid communication with the pipette; and a magnet disposed within the imaging chamber for preparing the specimen for imaging, wherein the magnet is configured to spread at least a portion of the specimen within the imaging chamber.

2. The assembly according to claim 1, wherein the microorganism specie includes an acid-fast *bacillus*.

3. The assembly according to claim 1, wherein the pipette is configured to be in fluid communication with the imaging cartridge upon depression of the sampling chamber.

4. The assembly according to claim 1, wherein the shaft includes at least two graduation marks indicating a minimum and a maximum volume, the graduation marks being configured for measuring an amount of the specimen.

5. The assembly according to claim 1, wherein the magnet is configured to move from one end of the imaging chamber to an opposite end of the imaging chamber for spreading the specimen therein.

6. The assembly according to claim 5 further comprising:
a plurality of rails disposed within the imaging chamber, wherein the rails are configured to support the magnet thereon.

7. An imaging cartridge for preparing a specimen for determining an amount of at least one microorganism specie, the imaging cartridge comprising:
a pipette dock configured to couple to a pipette containing a specimen such that the specimen is bio-contained therein;
at least one reagent for preparing the specimen for imaging;
an imaging chamber configured to be in fluid communication with the pipette; and
a magnet disposed within the imaging chamber for preparing the specimen for imaging, wherein the magnet is configured to spread at least a portion of the specimen within the imaging chamber.

8. The imaging cartridge according to claim 7, further comprising at least one valve disposed between the imaging chamber and the pipette, the at least one valve configured to allow a specimen to flow from the pipette to the imaging cartridge when the pipette is coupled to the imaging cartridge.

9. The imaging cartridge according to claim 7, further comprising at least one channel defined between the imaging chamber and the pipette, the channel configured to provide for fluid communication therebetween.

10. The imaging cartridge according to claim 7, further comprising a cartridge blister chamber in fluid communication with the imaging chamber.

11. The imaging cartridge according to claim 10, wherein the cartridge blister chamber further comprises a cartridge blister configured to release at least one decolorizer reagent therein when a force is applied to the cartridge blister.

12. The imaging cartridge according to claim 11, wherein the imaging cartridge further comprises a wicking chamber in fluid communication with the imaging chamber, the wicking chamber configured to remove excess decolorizer reagent from the imaging chamber.

13. The imaging cartridge according to claim 7, wherein the imaging cartridge further comprises indicia configured to provide information indicating an amount of specimen provided to the imaging chamber.

14. The imaging cartridge according to claim 7, wherein the imaging cartridge further comprises a porous imaging chamber cover, the porous imaging chamber cover configured to permit the specimen within the imaging chamber to dry and prevent bio-contaminants in the specimen from passing through the imaging chamber cover.

15. The imaging cartridge according to claim 14, wherein the imaging chamber cover comprises a hydrophobic membrane material.

16. The assembly according to claim 7, wherein the magnet is configured to move from one end of the imaging chamber to an opposite end of the imaging chamber for spreading the specimen therein.

17. The imaging cartridge according to claim 16 further comprising:
a plurality of rails disposed within the imaging chamber, wherein the rails are configured to support the magnet thereon.

18. An imaging cartridge for preparing a specimen for determining an amount of at least one microorganism specie, the imaging cartridge comprising:
a pipette dock configured to couple to a pipette containing a specimen such that the specimen is bio-contained therein;
at least one reagent for preparing the specimen for imaging;
an imaging chamber configured to be in fluid communication with the pipette, wherein the prepared specimen is configured to be spread in the imaging chamber for obtaining an image thereof; and
a magnet disposed within the imaging chamber, the magnet configured to move from one end of the imaging chamber to an opposite end of the imaging chamber for spreading the specimen therein.

* * * * *